United States Patent
Ogawa

(10) Patent No.: US 7,282,026 B2
(45) Date of Patent: Oct. 16, 2007

(54) ENDOSCOPE SYSTEM INCLUDING PLURALITY OF TYPES OF OPTICAL ADAPTERS

(75) Inventor: Kiyotomi Ogawa, Hachioji (JP)

(73) Assignee: Olympus Corporation (JP)

( * ) Notice: Subject to any disclaimer, the term of this patent is extended or adjusted under 35 U.S.C. 154(b) by 337 days.

(21) Appl. No.: 10/612,365

(22) Filed: Jul. 1, 2003

(65) Prior Publication Data

US 2004/0030221 A1 Feb. 12, 2004

(30) Foreign Application Priority Data

Jul. 3, 2002 (JP) .............................. 2002-194910

(51) Int. Cl.
*A61B 1/06* (2006.01)
(52) U.S. Cl. ...................... 600/172; 600/175
(58) Field of Classification Search ................ 600/103, 600/109, 111, 118, 160, 166, 172, 175, 176, 600/181; 348/45, 65
See application file for complete search history.

(56) References Cited

U.S. PATENT DOCUMENTS 6,063,023 A 5/2000 Sakiyama

FOREIGN PATENT DOCUMENTS

| JP | 02-020817 | 1/1990 |
|---|---|---|
| JP | 2001-275934 | 10/2001 |
| JP | 2001-299693 | 10/2001 |
| JP | 2002-345738 | 12/2002 |

*Primary Examiner*—Rosiland Rollins
(74) *Attorney, Agent, or Firm*—Ostrolenk, Faber, Gerb & Soffen, LLP

(57) ABSTRACT

An endoscope system comprises an electronic endoscope, a plurality of types of optical adapters, a control device, and a display device. The electronic endoscope includes an imaging unit. The plurality of types of optical adapters includes a predetermined observational optical system and is freely detachably attached to the distal section of the electronic endoscope. The observational optical system incorporated in each optical adapter includes an identification section with which the type of optical adapter is identified. The control device is electrically connected to the electronic endoscope. The control device includes an optical adapter identification/verification block that detects and verifies an identification section which identifies the type of optical adapter, an image processing section that receives an imaging signal from an imaging unit so as to produce a video signal, a control section that manipulates an image signal produced by the image processing section and controls the electronic endoscope and external equipment. The display device receives the video signal sent from the control unit and displays an image represented by the video signal.

11 Claims, 22 Drawing Sheets

WHICH DO YOU WANT TO PERFORM?

1. COMPARATIVE MEASUREMENT

2. STEREOSCOPIC MEASUREMENT

WHICH DO YOU WANT TO USE?

1. DIRECT-VISION ADAPTER

2. SIDE-VISION ADAPTER

FIG.22A FIG.22B
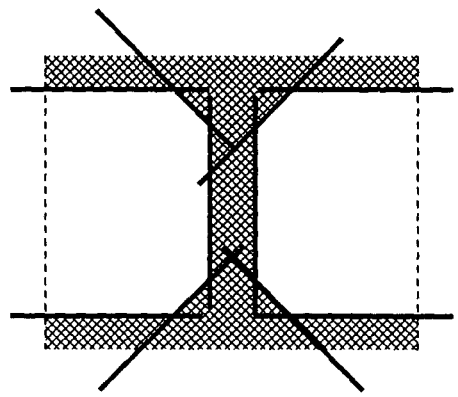
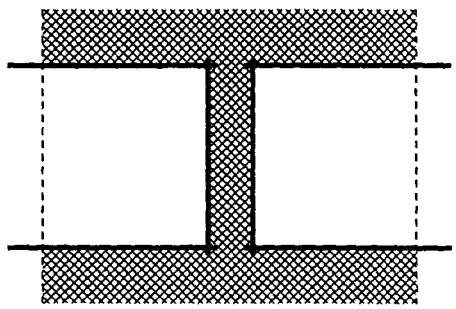
FIG.23A
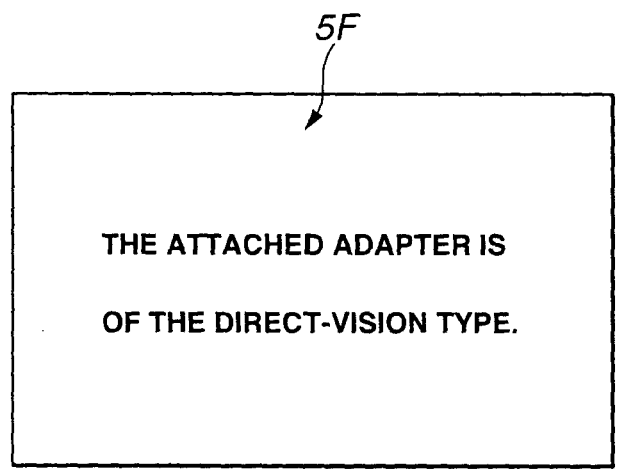
FIG.23B
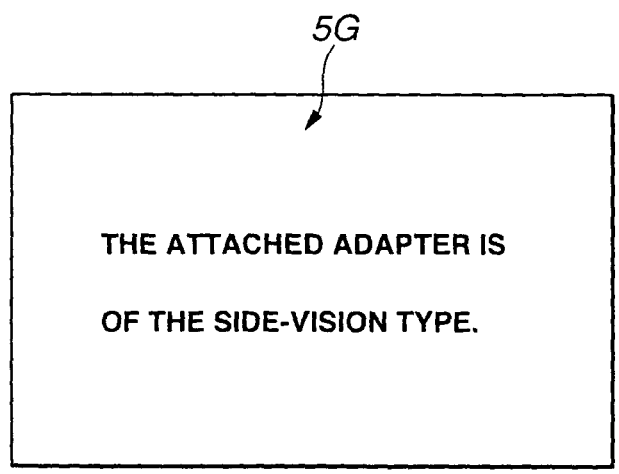

ENDOSCOPE SYSTEM INCLUDING PLURALITY OF TYPES OF OPTICAL ADAPTERS

This application claims the benefit of Japanese Application No. 2002-194910 filed on Jul. 3, 2002, the contents of which are incorporated by reference.

BACKGROUND OF THE INVENTION

1. Field of the Invention

The present invention relates to an endoscope system having a plurality of types of optical adapters selectively attached to an endoscope insertion unit for the purpose of observation.

2. Description of the Related Art

In recent years, endoscopes having an elongated insertion unit thereof inserted into a body cavity in order to observe an intracavitary organ or the like or perform various kinds of cures or treatments using, if necessary, treatment instruments passed through a treatment instrument channel have been widely utilized. In the field of industries, endoscopes for industrial use have been widely used to observe or inspect the interior of a boiler, a turbine, an engine, a chemical plant, or the like so as to see if the interior is flawed or corroded.

The endoscopes for the foregoing use include an electronic endoscope (hereinafter, simply, endoscope) having an imaging device that photoelectrically converts an optical image into an image signal, such as, a CCD incorporated in the distal section of the insertion unit. In the endoscope, an image processing unit produces a video signal from the image signal representing a view image picked up by the imaging device, and transmits the video signal to a monitor. Consequently, an endoscopic image is displayed on the screen of the monitor in order to enable observation.

In particular, the endoscope for industrial use has a plurality of types of optical adapters made ready to achieve observation according to a position to be inspected. The optical adapters are dedicated to, for example, direct-vision observation or side-vision observation, large-diameter or small-diameter tubes, or stereoscopic observation for which an observational optical system offers two observational fields of view. The optical adapters can be freely detachably attached to the distal section of the endoscope insertion unit, if necessary. For example, a measuring endoscope system disclosed in Japanese Unexamined Patent Application Publication No. 2001-275934 has various optical adapters attached to an insertion unit thereof according to a position of endoscopic inspection or a purpose thereof.

SUMMARY OF THE INVENTION

An endoscopic system comprises: an electronic endoscope having an imaging unit; a plurality of types of optical adapters freely attachable or detachable to or from the distal section of an insertion unit of the electronic endoscope; a control device including an optical adapter identifying/verifying means, an image processing means, and a control means, and a display device that receives a video signal from the control device and displays an image represented by the video signal.

Each of the optical adapters includes a predetermined observational optical system that has an identification section which identifies the type of optical adapter. The control device is electrically connected to the electronic endoscope.

The optical adapter identifying/verifying means included in the control device detects the identification section provided in the observational optical system included in an optical adapter so as to verify the type of optical adapter. Moreover, the image processing means receives an imaging signal from the imaging unit incorporated in the electronic endoscope and produces a video signal from the imaging signal. Furthermore, the control means manipulates an image signal produced by the image processing means or controls the electronic endoscope and external equipment.

The above and other objects and features of the invention, and the advantages thereof will become more clearly understood from the following description made by referring to the accompanying drawings.

BRIEF DESCRIPTION OF THE DRAWINGS

FIG. 1 to FIG. 23B are explanatory diagrams concerning a first embodiment of the present invention;

FIG. 1 is an explanatory diagram showing an endoscope system;

FIG. 2 is a block diagram showing the configuration of the endoscope system;

FIG. 3 is an explanatory diagram showing a remote controller;

FIG. 4 is a perspective view showing a direct-vision stereoscopic optical adapter attached to the distal section of an insertion unit;

FIG. 5 is a 5—5 sectional view of the adapter shown in FIG. 4;

FIG. 6 is an explanatory diagram concerning a field mask included in the direct-vision stereoscopic optical adapter;

FIG. 7 shows an endoscopic image rendering a region to be observed that is imaged via the direct-vision stereoscopic optical adapter;

FIG. 8 is a perspective view showing a side-vision stereoscopic optical adapter attached to the distal section of the insertion unit;

FIG. 9 is a 9—9 sectional view of the adapter shown in FIG. 8;

FIG. 10 is an explanatory diagram concerning a field mask included in the side-vision stereoscopic optical adapter;

FIG. 11 shows an endoscopic image rendering a region to be observed that is imaged through the side-vision stereoscopic optical adapter;

FIG. 12 is a flowchart describing a sequence that permits observation to be performed using the endoscope system;

FIG. 13 is a flowchart describing execution of measurement designation mentioned in FIG. 12;

FIG. 14 is an explanatory diagram showing a measurement selection screen image;

FIG. 15 is an explanatory diagram showing an adapter selection screen image;

FIG. 16 is a flowchart describing execution of measurement mentioned in FIG. 12;

FIG. 17 is a flowchart describing a sequence of adapter selection and check;

FIG. 19 is an explanatory diagram showing a first warning display image;

FIG. 21 is a flowchart describing a sequence for verifying an optical adapter;

FIG. 22A is an explanatory diagram concerning detection of the linear edges of the field mask included in the direct-vision stereoscopic optical adapter;

FIG. 22B is an explanatory diagram concerning detection of the linear edges of the field mask included in the side-vision stereoscopic optical adapter;

FIG. 23A is an explanatory diagram showing a screen image notifying that the direct-vision stereoscopic optical adapter is attached to the insertion unit;

FIG. 23B is an explanatory diagram showing a screen image notifying that the side-vision stereoscopic optical adapter is attached to the insertion unit;

FIG. 24A to FIG. 25 show or describe a structure or a procedure for checking the width of the openings of an optical adapter so as to verify the type of optical adapter;

FIG. 24A is an explanatory diagram showing a field mask whose openings have a large width and which is adapted to a direct-vision optical adapter;

FIG. 25 is a flowchart describing a sequence for verifying an optical adapter shown in FIG. 24A or FIG. 24B;

FIG. 26A to FIG. 28 show or describe a structure or a procedure for verifying the type of optical adaptor by matching an image of an optical adapter with a template;

FIG. 26A is an explanatory diagram showing a field mask that has a projection indicating a direct-vision optical adapter;

FIG. 28 is a flowchart describing a sequence for verifying the optical adapter shown in FIG. 26A or FIG. 26B;

FIG. 29A to FIG. 30 are explanatory diagrams showing or describing another structure or procedure for verifying the type of optical adapter by matching an image of an optical adapter with a template;

FIG. 29A is an explanatory diagram showing a field mask that has a projection indicating a direct-vision optical adapter;

FIG. 30 is a flowchart describing a sequence for verifying the optical adapter shown in FIG. 29A or FIG. 29B;

FIG. 31A is an explanatory diagram showing the position of a projection indicating a direct-vision optical adapter;

FIG. 31B is an explanatory diagram showing the position of a projection indicating a side-vision optical adapter;

FIG. 32 is a block diagram showing another configuration of an endoscope system;

FIG. 33 is a flowchart describing a sequence permitting observation to be performed using the endoscope system; and FIG. 34 is an explanatory diagram describing a sequence of adapter verification and information specification.

DESCRIPTION OF THE PREFERRED EMBODIMENTS

An endoscope system of a first embodiment will be described with reference to the drawings below.

Figure 1:
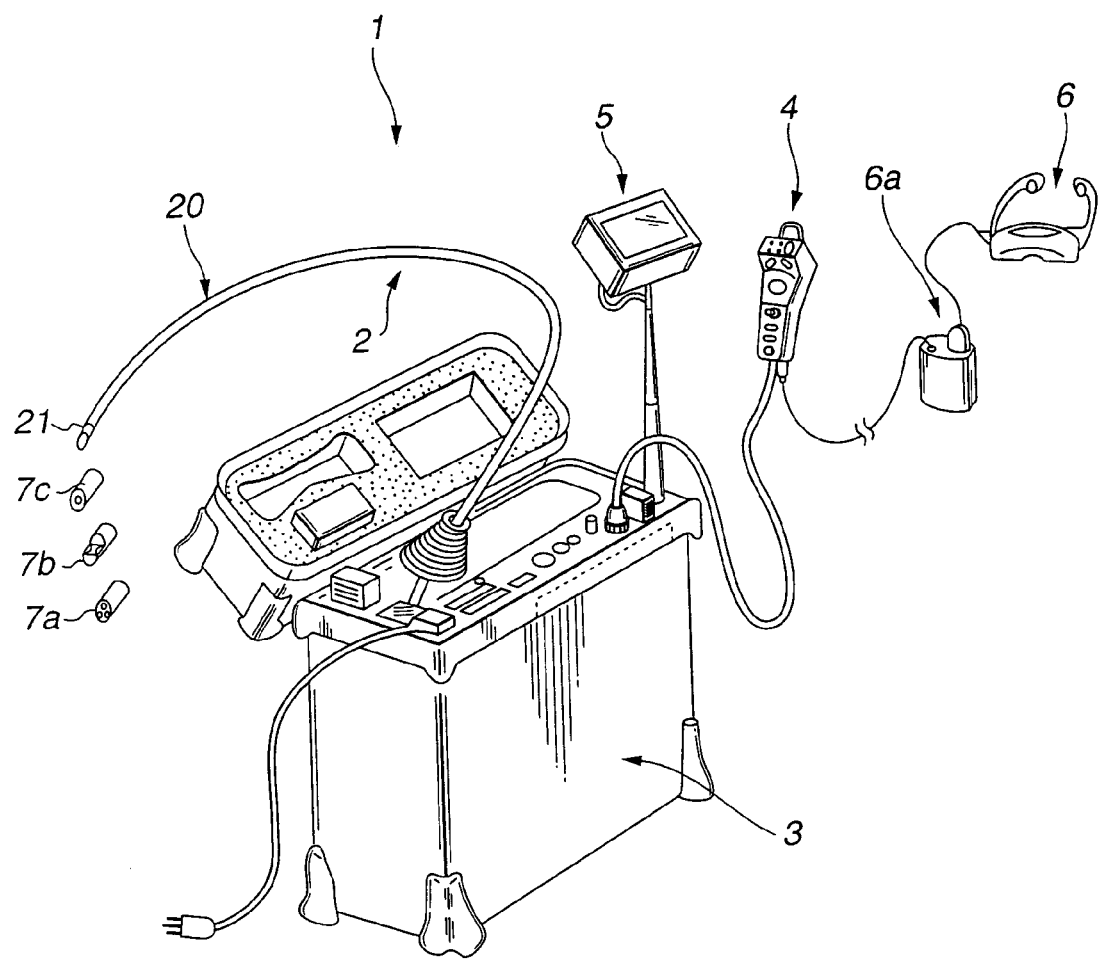

As shown in FIG. 1, an endoscope system 1 for use of measurement comprises an endoscope 2, a control unit 3 that is a control device, a remote controller 4, a liquid crystal display (hereinafter LCD) 5 that is a display device, and a face-mounted display (hereinafter FMD) 6.

The endoscope 2 has an elongated insertion unit 20. The control unit 3 has a storage chamber in which the insertion unit 20 is stored. Using the remote controller 4, the entire endoscope system 1 can be appropriately operated in order to execute various kinds of action control sequences. An endoscopic image or the contents of operation control (for example, a processing menu to be described later) are displayed on the LCD 5. The FMD 6 enables normal observation of an endoscopic image or enables stereoscopic observation by quasi-stereoscopically presenting the endoscopic image. The FMD 6 is provided with a FMD adapter 6a which supplies image data.

The insertion unit 20 has a hard distal section 21, a bending section 22 that can be bent, for example, vertically and horizontally, and a flexible tube 23 having flexibility concatenated in that order from the distal end thereof. Various types of optical adapters including stereoscopic optical adapters 7a and 7b each having two observational fields of view, and a normal observation optical adapter 7c having one observational field of view can be freely attached or detached to or from the distal section 21 by, for example, screwing the adapters to or off the distal section 21.

Figure 2:
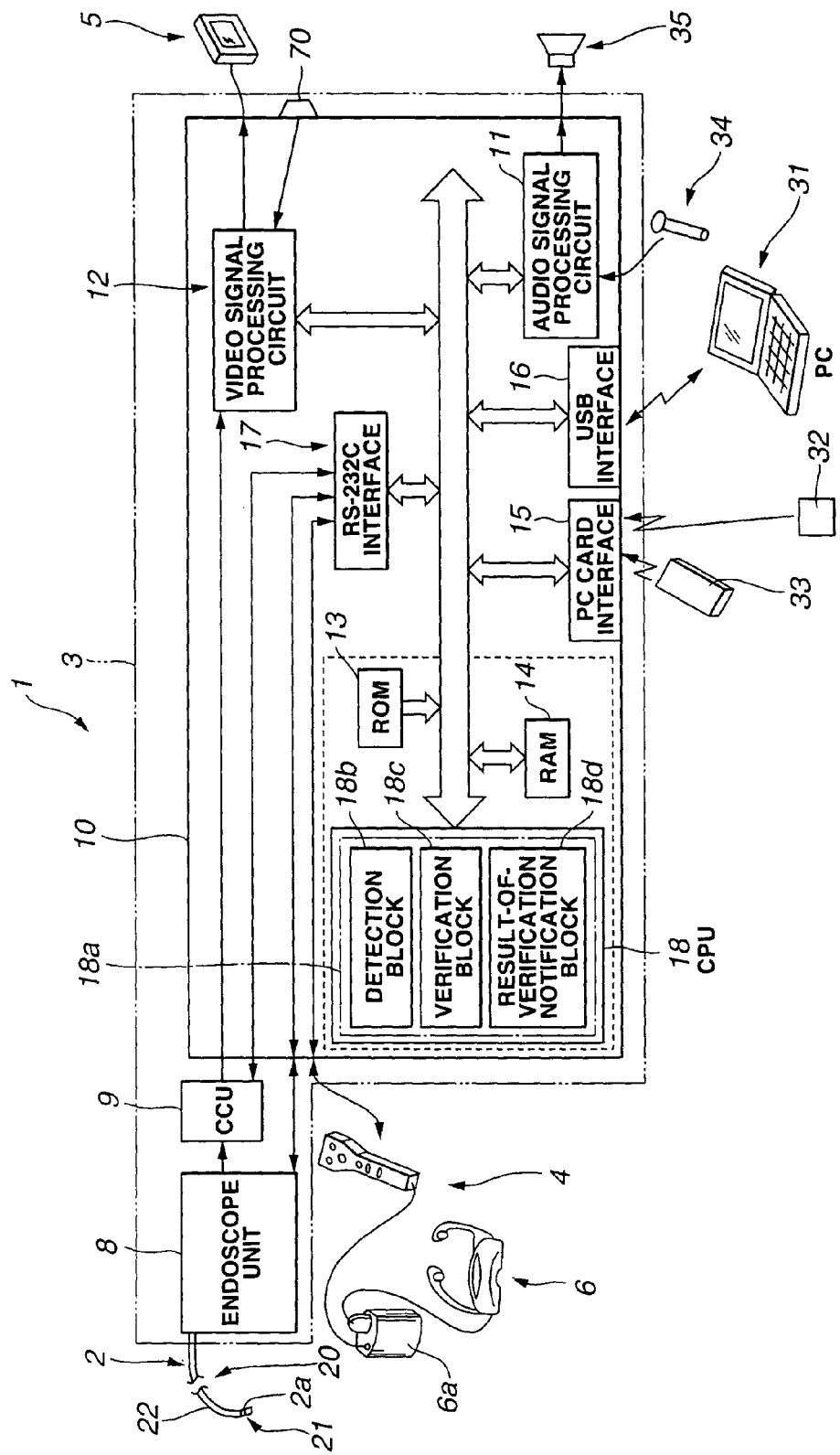

As shown in FIG. 2, an endoscope unit 8, a camera control unit (hereinafter CCU) 9 that is an image processing section, and a control section 10 are incorporated in the control unit 3. The proximal portion of the insertion unit 20 is coupled to the endoscope unit 8.

A light source device (not shown) for supplying required illumination light for observation, and a bending device (not shown) for bending the bending section 22 that is an integral part of the insertion unit 20 are incorporated in the endoscope unit 8.

The CCU 9 receives an imaging signal transmitted from a solid-state imaging device 2a incorporated in the distal section 21 of the insertion unit 20. The imaging signal is converted into a video signal, for example, an NTSC signal within the CCU 9 and transmitted to the control section 10.

The control section 10 includes an audio signal processing circuit 11, a video signal processing circuit 12 that receives the video signal, a ROM 13, a RAM 14, a PC card interface 15, a USB interface 16, and an RS-232C interface 17, and a CPU 18.

The CPU 18 executes various features according to a main program so as to control actions. Moreover, the CPU 18 includes an adapter identification block 18a that serves as an optical adapter identifying/verifying means for identifying the types of optical adapters 7a, 7b, 7c, etc.

The CCU 9, the endoscope unit 8, and the remote controller 4 that controls the CCU 9 and endoscope unit 8 and directs actions are connected to the RS-232C interface 17.

When the remote controller 4 is handled, a required control signal is transmitted to the CCU 9 and endoscope unit 8 according to the handling.

The USB interface 16 is an interface via which the control unit 3 and a personal computer 31 are electrically connected to each other. The control unit 3 and personal computer 31 are connected to each other via the USB interface 16, whereby various directive control signals or data can be transmitted or received. In other words, the personal computer 31 can be used to direct display of an endoscopic image or to direct or control image processing during measurement. Moreover, control information or data required for various kinds of processing can be transmitted or received between the control unit 3 and personal computer 31.

A so-called memory card that is a recording medium such as a PCMCIA memory card 32 or a compact flash® memory card 33 can be freely loaded or unloaded in or from the PC card interface 15.

When a memory card is loaded in the PC card interface 15, control information, image information, or any other data can be fetched from the memory card under the control of the CPU 18. Otherwise, control processing information, image information, or any other data can be recorded in the memory card.

The video signal processing circuit 12 performs the processing of displaying a synthetic image, which is produced by synthesizing an endoscopic image sent from the CCU 9 with an operation menu that is a graphic, on the LCD 5. Specifically, a video signal sent from the CCU 9 is synthesized with a display signal that is produced based on an operation menu under the control of the CPU 18, and processing required to display an image on the LCD 5 is carried out. Thereafter, the produced video signal is transmitted to the LCD 5. Incidentally, the video signal processing circuit 12 can perform the processing of displaying an endoscopic image or an operation menu graphic alone.

Consequently, an endoscopic image, an operation menu graphic, and a synthetic image of the endoscopic image and operation menu graphic are displayed on the screen of the LCD 5.

Various audio signals are transferred to the audio signal processing circuit 11. The audio signal processing circuit 11 performs amplification and other processing required to regenerate a received audio signal, and transmits the resultant audio signal to a loudspeaker 35. Consequently, the loudspeaker 35 radiates sounds. The audio signal is produced by collecting sounds through a microphone 34, read from a recording medium such as a memory card, regenerated from the recording medium such as a memory card, or produced by the CPU 18.

The CPU 18 runs a program stored in the ROM 13 so as to control various circuits. The CPU 18 thus performs processing according to a specific purpose and controls the actions of the entire system.

Figure 3:
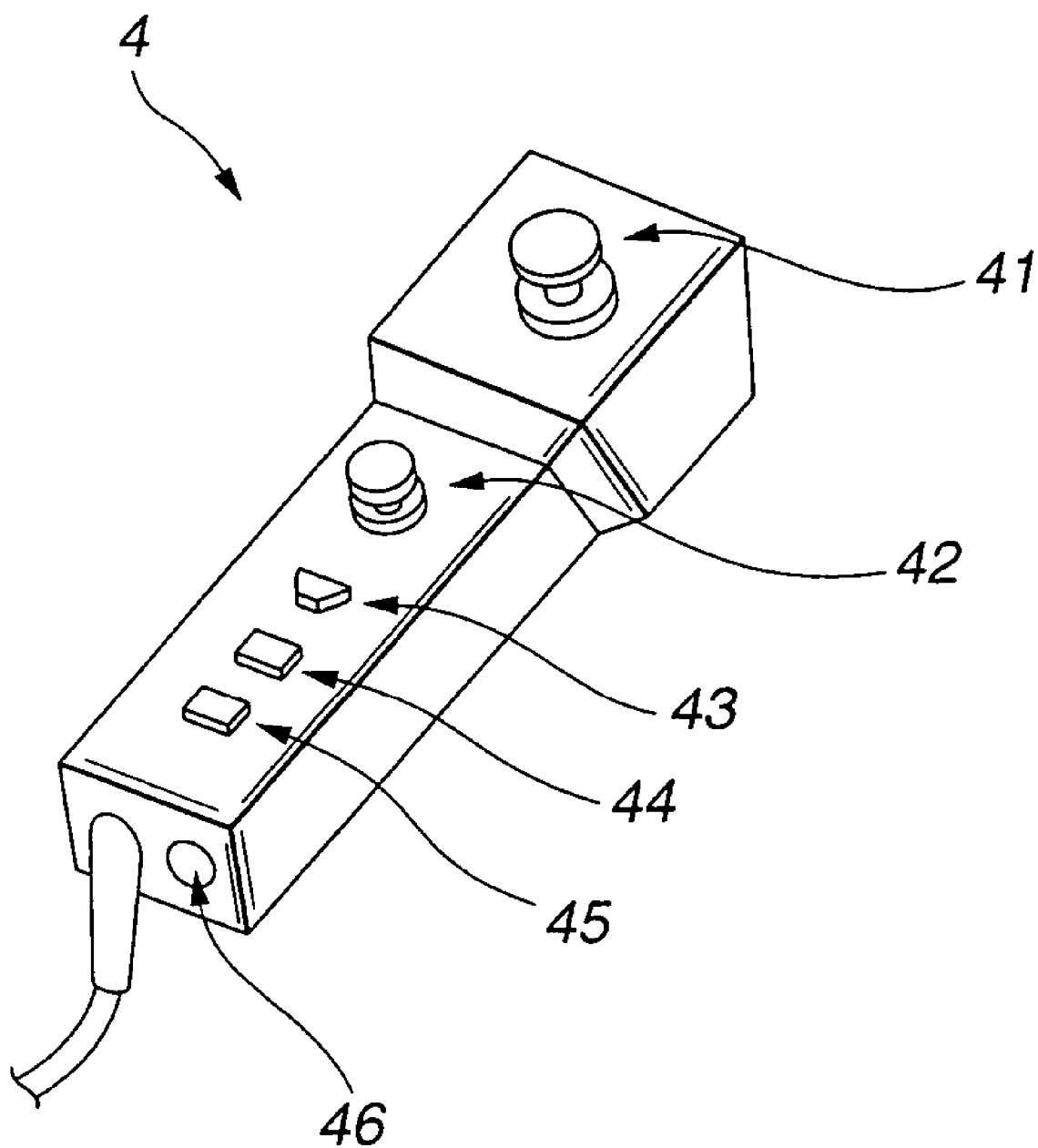

As shown in FIG. 3, a joystick 41, a lever switch 42, a Freeze switch 43, a Store switch 44, and a measurement execution switch 45 are disposed on one side of the remote controller 4.

The joystick 41 is a switch for use in directing the bending section 22 to bend. By tilting the joystick 41, the bending section 22 bends by an angle, by which the joystick is tilted, in a direction corresponding to the direction in which the joystick is tilted.

The lever switch 42 is a switch for use in manipulating various menus displayed as graphics or moving a pointer during measurement. The lever switch 42 has substantially the same structure as the joystick 41.

The Freeze switch 43 is a switch relevant to display of an image on the LCD 5.

The Store switch 44 is a switch for use in recording a still image, which is displayed by pressing the Freeze switch 43, in the memory card.

The measurement execution switch 45 is a switch for use in running measurement software.

The Freeze switch 43, Store switch 44, and measurement execution switch 45 are realized with, for example, push-button switches that are turned on or off when pressed.

Incidentally, reference numeral 46 denotes a connector to which an electric cable extending from an FMD adapter 7 is plugged. By plugging the electric cable to the connector 46, stereoscopic observation can be performed using the FMD 6.

Now, the structures of stereoscopic optical adapters that are included in the optical adapters employed in the endoscope system 1 of the present embodiment will be described with reference to FIG. 4 to FIG. 11.

The stereoscopic optical adapters fall into a direct-vision type shown in FIG. 4 to FIG. 7 and a side-vision type shown in FIG. 8 to FIG. 11. Incidentally, the optical adapter 7a is of the direct-vision type, and the optical adapter 7b is of the side-vision type.

Figure 4:
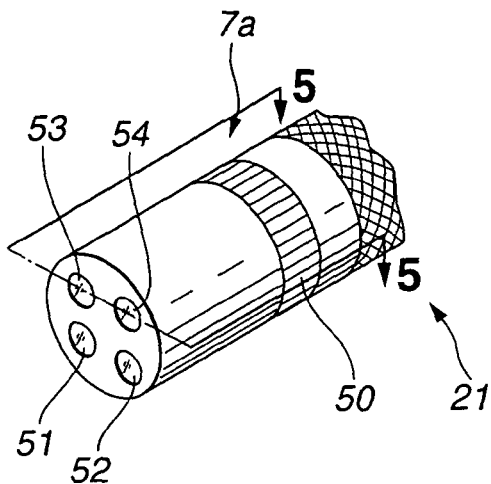
Figure 5:
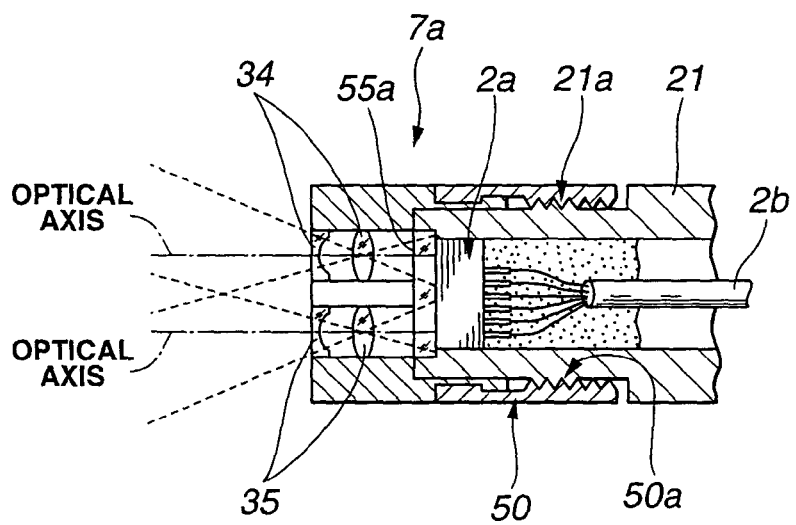

As shown in FIG. 4 and FIG. 5, a pair of illumination lenses 51 and 52 and two systems of objectives 53 and 54 are bared on the distal surface of the direct-vision stereoscopic optical adapter 7a. The stereoscopic optical adapter 7a and distal section 21 are joined as a united body when screwed to each other. Specifically, a female screw 50a threaded on a locking ring 50 that is freely rotatively included in the stereoscopic optical adapter 7a is meshed with a male screw 21a threaded on the internal surface of the distal section 21. Thus, the stereoscopic optical adapter 7a can be freely detachably attached to the distal section 21.

Figure 6:
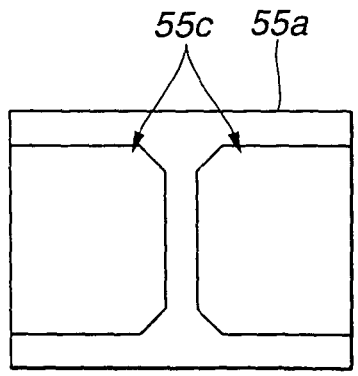

As shown in FIG. 5 and FIG. 6, a field mask 55a having two hexagonal openings 55c is located proximally to the two systems of objectives 53 and 54. Two optical images having passed through the openings 55c of the field mask 55a are therefore formed on the imaging surface of the solid-state imaging device 2a incorporated in the distal section 21.

An imaging signal photoelectrically converted by the solid-state imaging device 2a is transmitted to the CCU 9 by way of the signal line 2b, which is electrically coupled to the solid-state imaging device, and the endoscope unit 8, and converted into a video signal. The video signal is transmitted to the video signal processing circuit 12.

Figure 7:
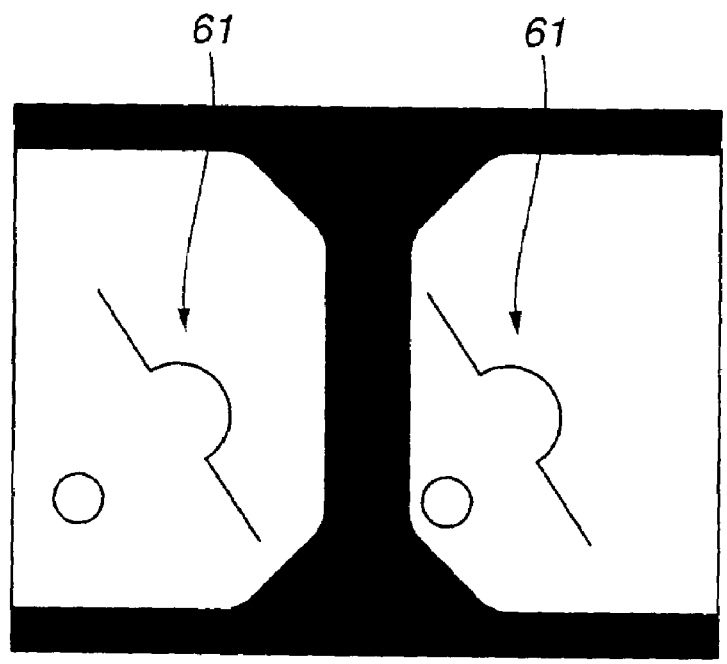

Consequently, the images of the two hexagonal openings and the images 61 that render a region to be observed and are located in the respective images of the openings are, as shown in FIG. 7, displayed on the screen of the LCD 5.

Figure 8:
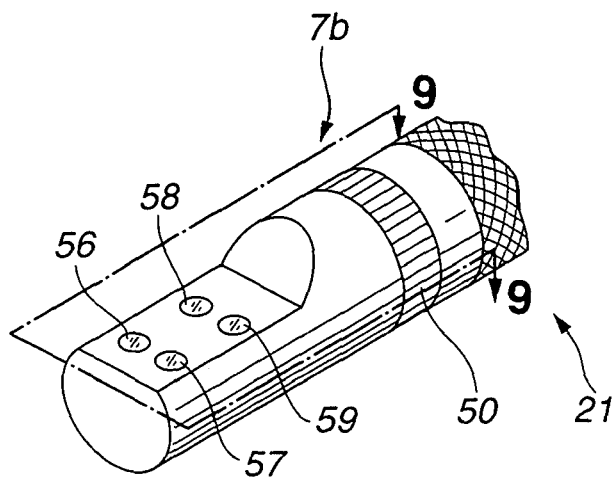

On the other hand, for example, a pair of illumination lenses 56 and 57 and two systems of objectives 58 and 59 are, as shown in FIG. 8, bared on the distal surface of the side-vision stereoscopic optical adapter 7b. Similarly to the aforesaid direct-vision stereoscopic optical adapter, the side-vision stereoscopic optical adapter 7b is firmly screwed to the distal section 21 by meshing the female screw 50a threaded on the locking ring 50 with the male screw 21a threaded on the internal surface of the distal section 21.

Figure 9:
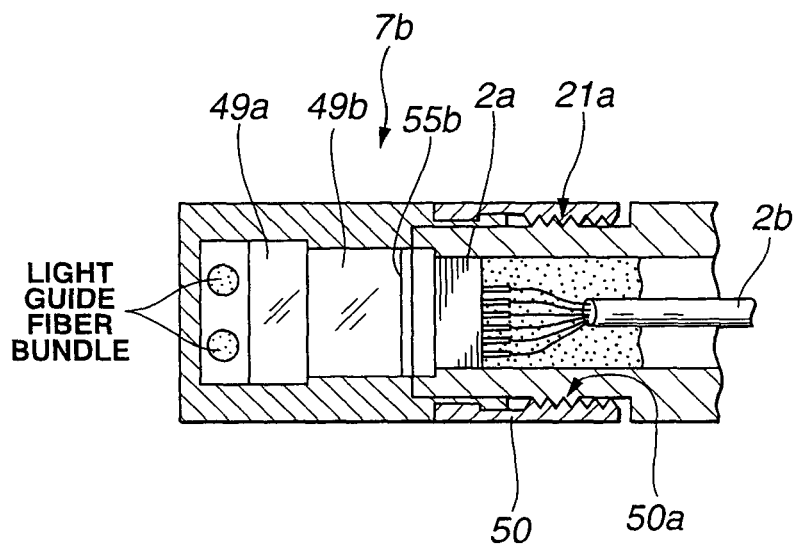
Figure 10:
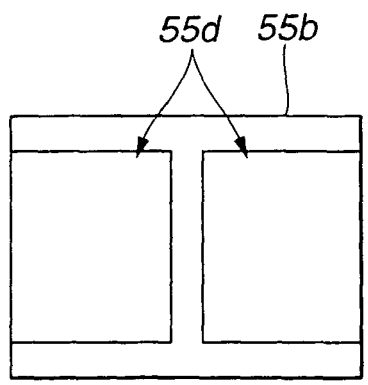

As shown in FIG. 9, a prism 49a and an optical lens 49b that bend a ray axis 90° are located immediately below the two systems of objectives 58 and 59. A field mask 55b is located proximally to the optical lens 49b. As shown in FIG. 10, the field mask 55b has two rectangular openings 55d.

Consequently, two optical images having passed through the openings 55d of the field mask 55b are formed on the imaging surface of the solid-state imaging device 2a incorporated in the distal section 21.

An imaging signal photoelectrically converted by the solid-state imaging device 2a is transmitted to the CCU 9 by way of the signal line 2b, which is electrically coupled to the solid-state imaging device, and the endoscope unit 8, and converted into a video signal. The video signal is transmitted to the video signal processing circuit 12.

Figure 11:
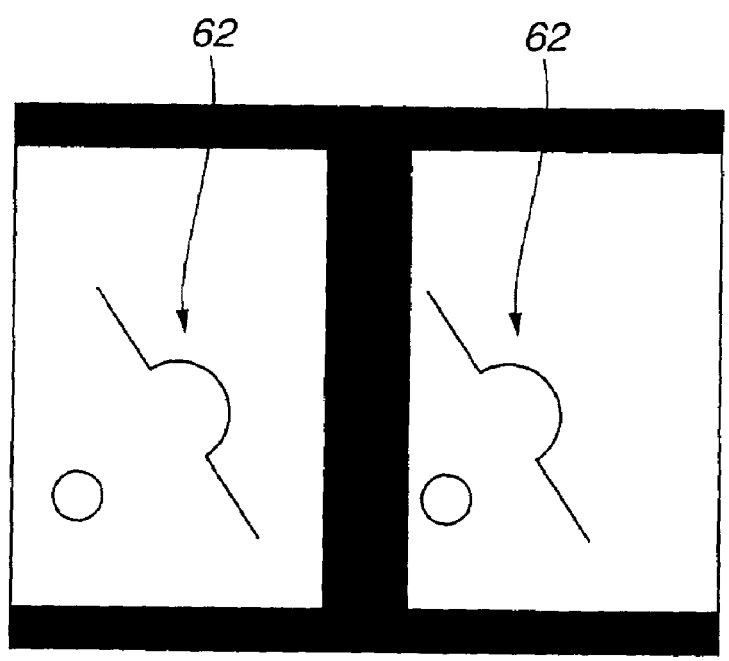

The images of the two rectangular openings and the images 62 that render a region to be observed and lie in the respective images of the openings are, as shown in FIG. 11, displayed on the screen of the LCD 5.

According to the present embodiment, as apparent from FIG. 7 and FIG. 11, the shapes of the two openings of the field masks 55a and 55b located in the respective observational optical systems included in the direct-vision stereoscopic optical adapter 7a and side-vision stereoscopic optical adapter 7b respectively are different from each other.

In other words, the shapes of the openings of the field masks 55a and 55b serve as identification sections which identifies the optical adapters. By determining whether the shape of the openings is hexagonal or rectangular, it is recognized whether the optical adapter is of the direct-vision type or side-vision type.

When the endoscope system 1 of the present embodiment is used to perform stereoscopic measurement, the endoscopic images 61 or 62 shown in FIG. 7 or FIG. 11 is employed. At this time, the CPU 18 fetches adapter information concerning the direct-vision stereoscopic optical adapter 7a or side-vision stereoscopic optical adapter 7b, and executes stereoscopic measurement processing according to the fetched adapter information.

For normal measurement, adapter information concerning a normal optical adapter is fetched, and normal measurement processing is executed based on the fetched adapter information. The adapter information is stored in the ROM 13 or any other recording medium.

Now, a description will be made of stereoscopic measurement to be performed using the endoscope system 1 having the foregoing components.

For example, the direct-vision stereoscopic optical adapter 7a is attached as a desired optical adapter to the distal section 21 of the endoscope 2. In this state, the power supply of the endoscope system 1 is turned on. The CPU 18 performs initialization, and then runs a main program.

Figure 12:
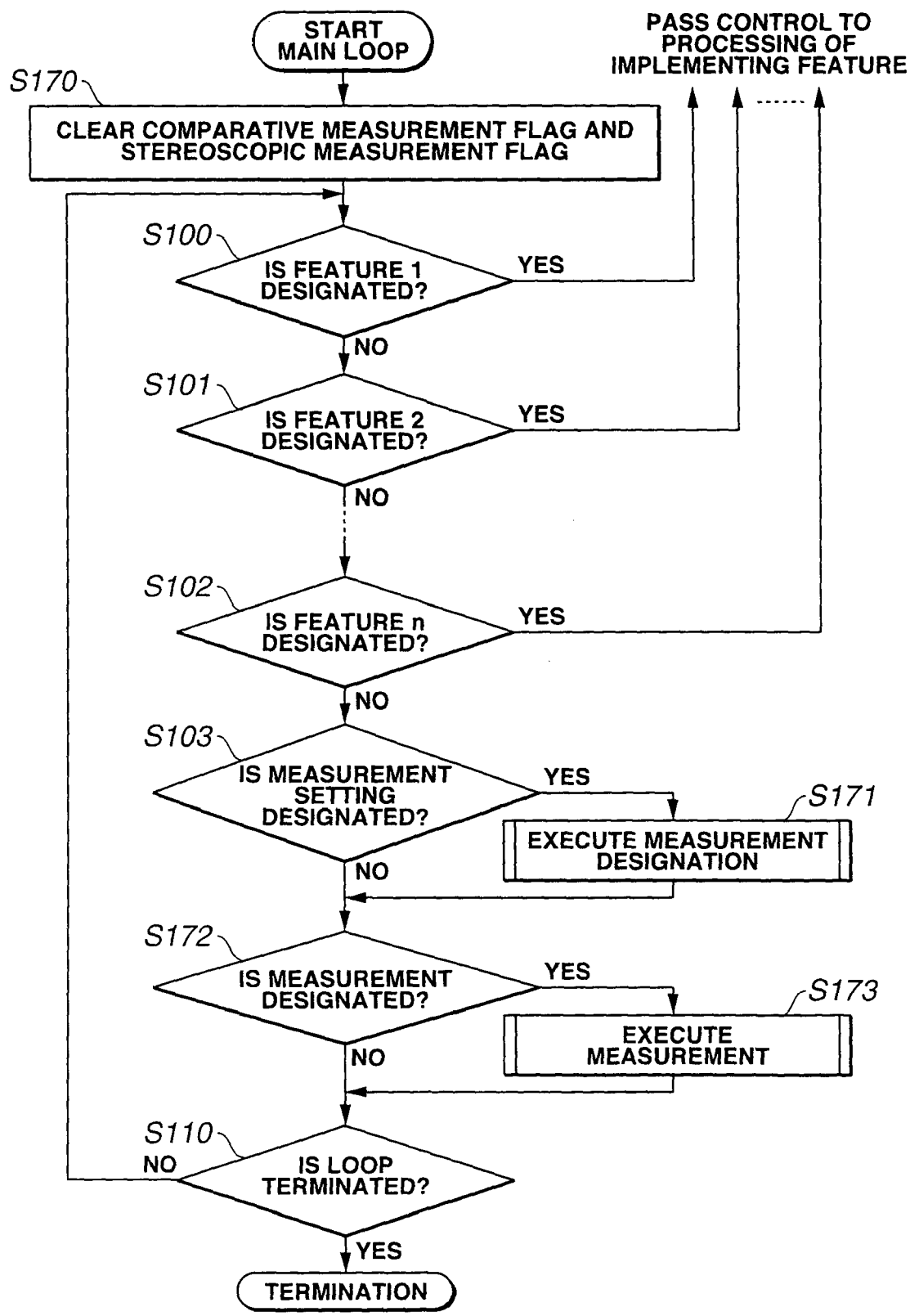

As described in FIG. 12, after flags are cleared at step S170, a standby state is established for a main loop composed of decision steps S100, S101, S102, S103, S172, and S110.

Figure 13:
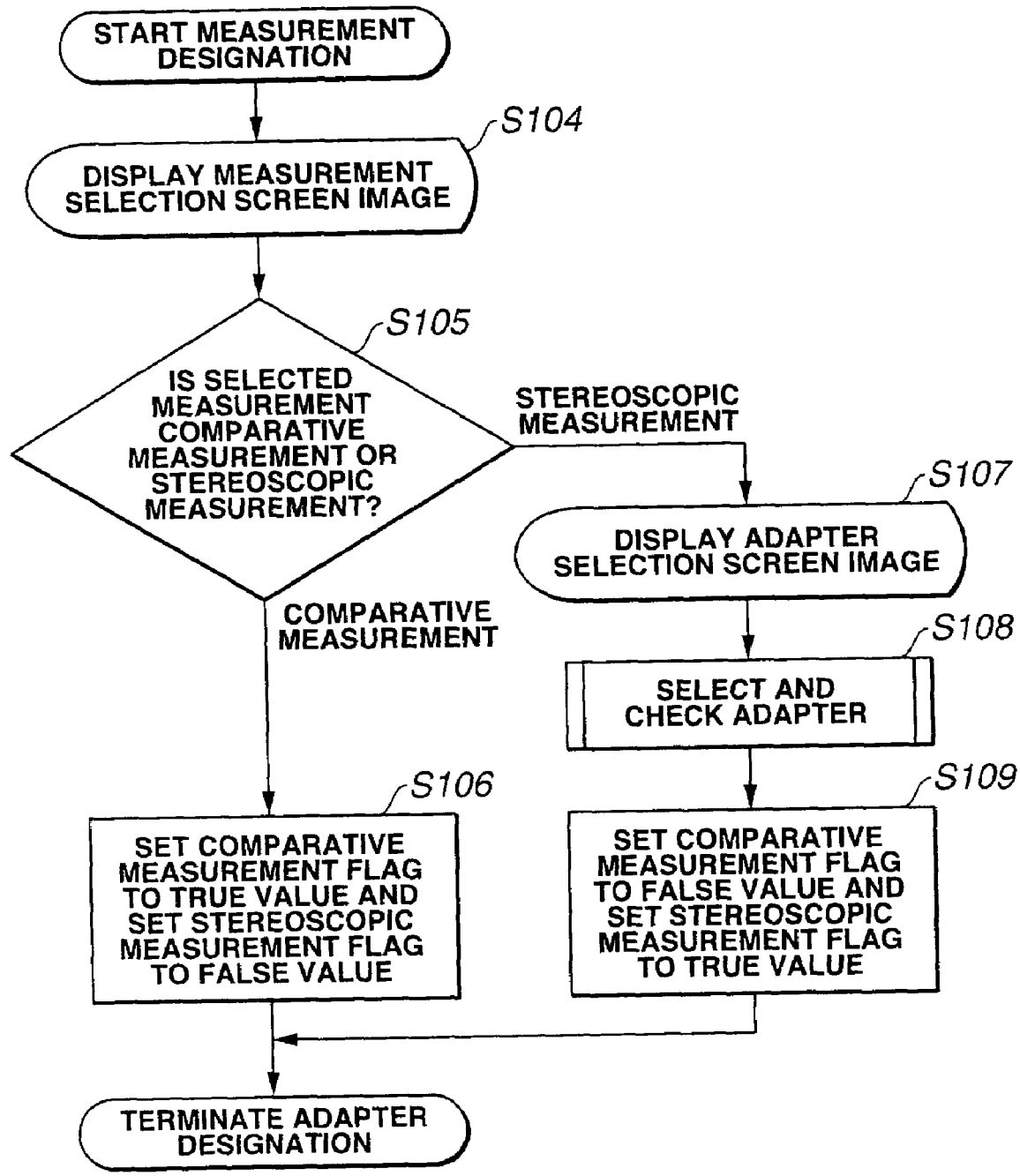

When a feature is designated at each of the steps S100, S101, and S102, the CPU 18 passes control to the processing that implements the designated feature. When a feature is designated at step S103, control is passed from step S171 to step S104 described in FIG. 13. A measurement selection screen image 5A (hereinafter, a selection screen image) like the one shown in FIG. 14 appears on the screen of the LCD 5. When the selection screen image 5A is displayed, a user selects normal measurement or stereoscopic measurement at step S105.

Assuming that the user selects normal measurement, an optical adapter to be employed is the normal observation optical adapter 7c. At the next step S106, a comparative measurement flag is set to a TRUE value and a stereoscopic measurement flag is set to a FALSE value. Control is then passed to the main loop.

On the other hand, when stereoscopic measurement is selected at step S105, control is passed to step S107. The image displayed on the screen of the LCD 5 is changed to an adapter selection screen image 5B shown in FIG. 15. The user is then prompted to select any item. Thereafter, control is passed to step S108. Adapter selection and attachment that will be described later is executed. It is then checked if the optical adapter attached to the insertion unit 20 agrees with the adapter selected at step S107. When the adapters agree with each other, the stereoscopic measurement flag is set to the TRUE value at the next step S109, and the comparative measurement flag is set to the FALSE value. Control is then passed to the main loop.

Figure 16:
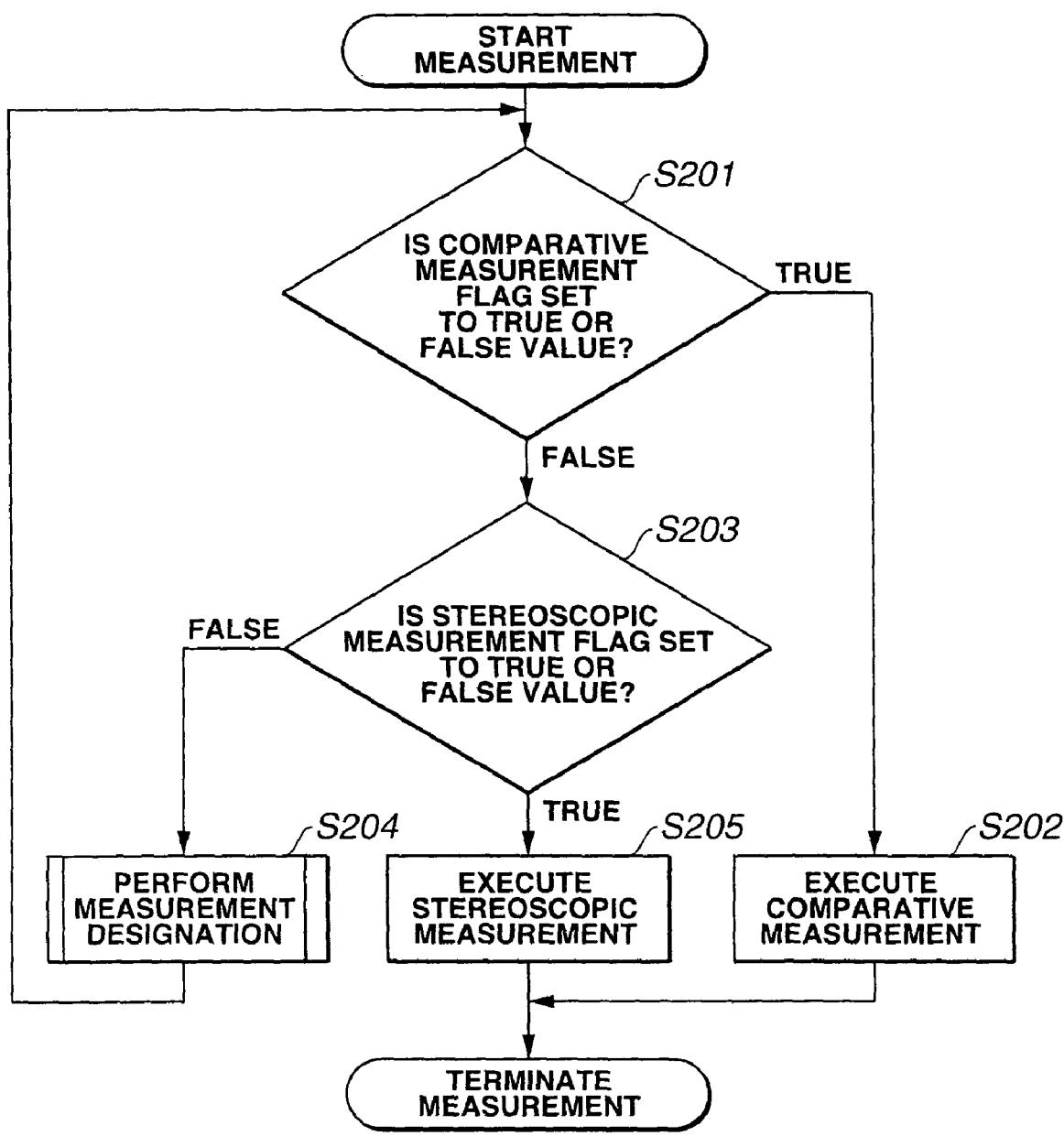

When the measurement execution switch 45 is pressed, it is determined that measurement is designated at step S172. Control is passed from step S173 to step S201 described in FIG. 16. The value of the comparative measurement flag is then determined. When it is determined that the comparative measurement flag is set to the TRUE value, control is passed to step S202. Comparative measurement is then executed. Thereafter, measurement processing is terminated and control is returned to the main loop.

On the other hand, when it is determined at step S201 that the comparative measurement flag is set to the FALSE value, control is passed to step S203 and the stereoscopic measurement flag is determined. When it is determined that the stereoscopic measurement flag is set to the FALSE value, control is passed from step S204 to step S104. Measurement designation processing is then performed. After measurement designation processing is terminated, the processing that starts at step S201 is resumed.

When it is determined at step S203 that the stereoscopic measurement flag is set to the TRUE value, control is passed to step S205 and stereoscopic measurement processing is executed. Thereafter, measurement processing is terminated and control is returned to the main loop.

When measurement processing is not selected at step S103, control is passed to step S110. It is determined whether handling for termination is performed. When the CPU 18 determines that the handling for termination is performed, the CPU 18 starts termination processing. Otherwise, control is returned to step S100.

After measurement processing is selected at step S103, control may be passed to the main loop. In this case, the CPU 18 extends control so that the endoscope system 1 will be placed in a standby state until the user presses the measurement execution switch 45 on the remote controller 4. Thereafter, when the user presses the measurement execution switch 45 on the remote controller 4, the CPU 18 runs the program to perform measurement.

Figure 17:
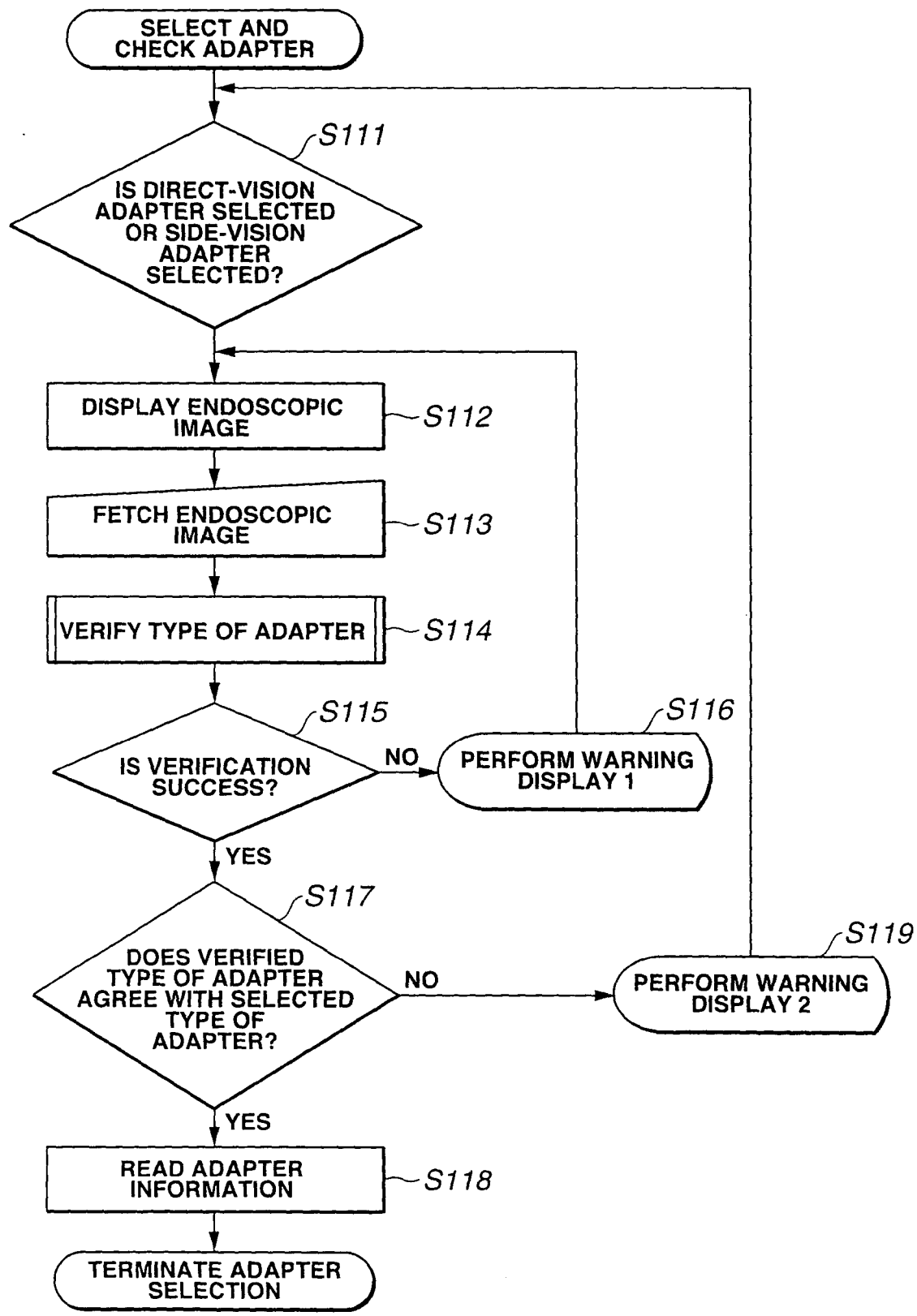

Now, referring to FIG. 17, a sequence of adapter selection and check will be described below.

The adapter identification block 18a included in the CPU 18 shown in FIG. 2 includes a detection block 18b, an adapter type verification block 18c, and a result-of-verification notification block 18d. The detection block 18b detects the shape of the openings of a field mask. The adapter type verification block 18c verifies the type of optical adapter from the result of detection received from the detection block 18b. The result-of-verification notification block 18d is a result-of-verification notifying means for notifying a user of the result of verification received from the adapter type verification block 18c.

At step S107, the adapter selection screen image 5B is displayed. Control is then passed to step S108 of adapter selection and check. As described at step S111 in FIG. 17, the user selects direct-vision observation or side-vision observation.

Figure 18A:
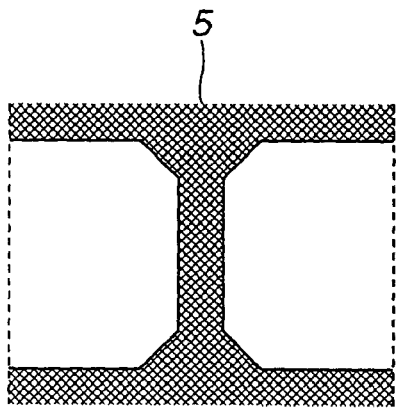
FIG. 18A shows an endoscopic image rendering a field mask included in the direct-vision stereoscopic optical adapter.
Figure 18B:
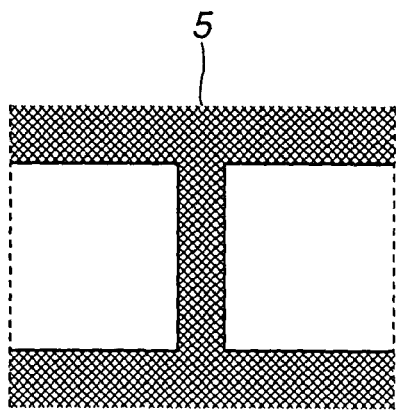
FIG. 18B shows an endoscopic image rendering a field mask included in the side-vision stereoscopic optical adapter.

At step S112, an endoscopic image of the field mask included in the stereoscopic optical adapter 7a or 7b attached to the distal section 21 is, as shown in FIG. 18A or FIG. 18B, displayed on the screen of the LCD 5. Control is then passed to step S113. When the user handles a Fetch button 70, the endoscopic image is fetched.

In the present embodiment, as mentioned above, the direct-vision stereoscopic optical adapter 7a is attached as a desired optical adapter to the distal section 21. Consequently, the endoscopic image shown in FIG. 18A is displayed on the screen of the LCD 5.

After the endoscopic image of the field mask is displayed on the screen of the LCD 5, when fetching the image is completed, control is passed to step S114. Adapter type verification that will be described later is then started.

At step S114, the shape of the openings of the field mask is detected at the direction of the detection block 18b. Based on the result of the detection, the adapter type verification block 18c verifies the type of adapter. Thereafter, it is checked at step S115 whether adapter type verification has succeeded.

Figure 19:
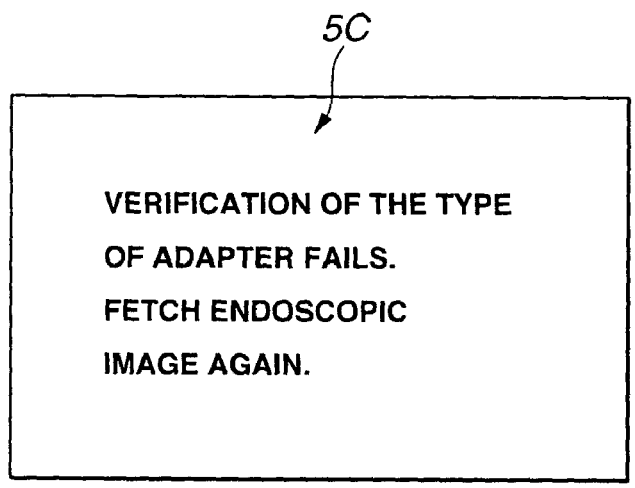

When it is found at step S113 that adapter type verification fails for some reason, that is, because of a failure in fetching of a white image or the like, a first warning display image 5C for notifying a user of re-fetching as shown in FIG. 19 is displayed on the screen of the LCD 5 at step S116. Control is then returned to step S112.

Figure 20A:
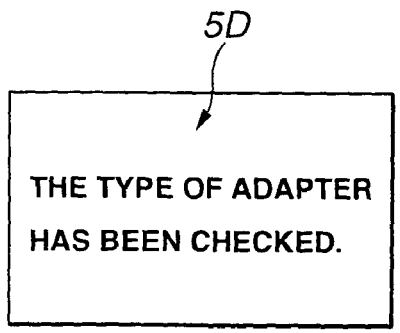
FIG. 20A is an explanatory diagram showing a screen image notifying start of measurement.

On the other hand, when adapter type verification has succeeded, control is passed to step S117. At step S117, it is checked whether the type of adapter verified at step S114 agrees with the type of adapter the user has selected at step S111. When the verified type of adapter agrees with the user-selected type of adapter, a notification screen image 5D shown in FIG. 20A is displayed for the user. Adapter selection and check is then terminated.

Figure 20B:
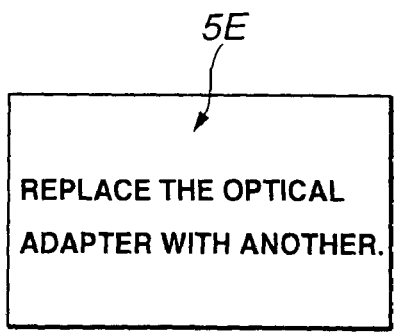
FIG. 20B is an explanatory diagram showing a second warning display image.

When it is found at step S117 that the user-selected type of adapter disagrees with the verified type of adapter, control is passed to step S119. A second warning display image 5E for notifying, as shown in FIG. 20B, that the optical adapter should be replaced with another is displayed on the screen of the LCD 5 via the result-of-verification notification block 18d. Control is then returned to step S111.

Figure 21:
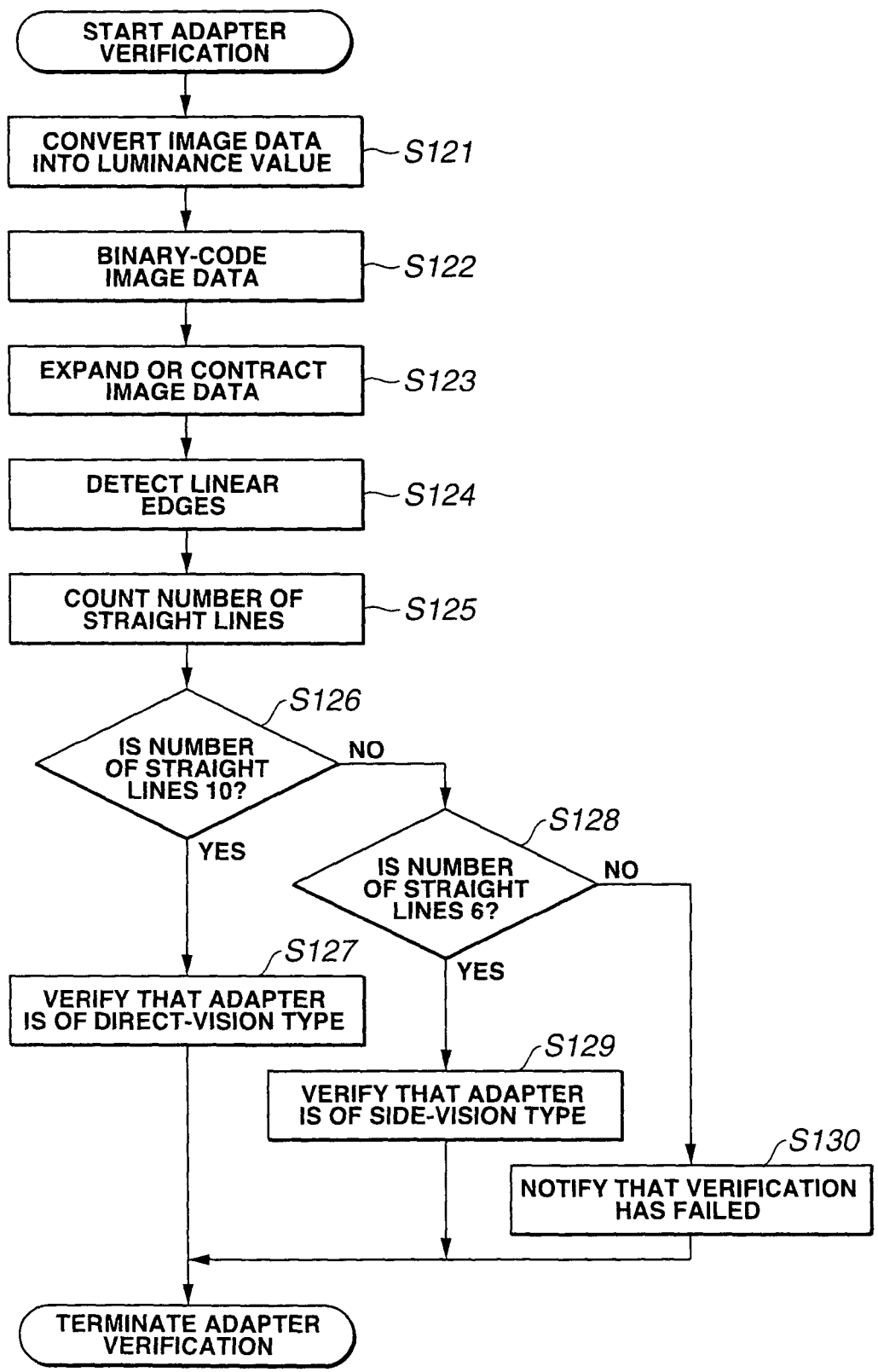

Referring to FIG. 21, adapter type verification will be described in a concrete manner.

After image fetch is executed at step S113, control is passed to step S114 of adapter type verification. The adapter identification block 18a identifies and verifies an adapter at the direction of the detection block 18b.

At this time, at steps S121 to S123 in FIG. 21, the endoscopic image fetched at the direction of the detection block 18b is converted into luminance values, binary-coded, and expanded or contracted. At step S124, linear edges are detected as shown in FIG. 22A. Thereafter, at step S125, the number of straight lines is counted, and processing is changed from that assigned to the detection block 18b to that assigned to the adapter type verification block 18c.

The adapter type verification block 18c verifies the type of adapter on the basis of reference values stored in the ROM 13. Specifically, first, at step S126, the number of straight lines is compared with a reference value of 10 that indicates the direct-vision type. When it is verified that the number of straight lines is 10, control is passed to step S127. A direct-vision adapter notification screen image 5F for notifying that the attached optical adapter is of the direct-vision type is, as shown in FIG. 23A, displayed on the screen of the LCD 5. Adapter type verification is then terminated and control is passed to step S115.

On the other hand, when it is verified at step S126 that the number of straight lines is not 10, the number of straight lines is compared at step S128 with a reference value of 6 that indicates the side-vision type as shown in FIG. 22B. When the number of straight lines is 6, control is passed to step S129. A side-vision adapter notification screen image 5G for notifying that the attached optical adapter is of the side-vision type is, as shown in FIG. 23B, displayed on the screen of the LCD 5. Adapter type verification is then terminated and control is passed to step S115.

When it is verified at step S128 that the number of straight lines is not 6, control is passed to step S130. Consequently, the first warning display image 5C for notifying that adapter verification has failed is, as shown in FIG. 19, displayed on the screen of the LCD 5. Adapter type verification is then terminated and control is passed to steps S115 and S116.

As mentioned above, when the user selects stereoscopic measurement, the user designates on the LCD whether the measurement should be performed through the direct-vision observation or the side-vision observation. Thereafter, the detection block, adapter type verification block, and result-of-verification notification block included in the CPU check the identification section of the optical adapter attached to the distal section of the insertion unit to see if the optical adapter is adaptable to the measurement selected by the operator. Thereafter, after it is checked if the selection of an optical adapter is correct, measurement work is carried out. Consequently, stereoscopic measurement can be reliably executed with the optical adapter adaptable to the user-intended stereoscopic measurement attached to the distal section of the insertion unit.

In the present embodiment, the type of optical adapter is verified based on the number of straight lines based on which the shapes of the openings of the field masks can be discriminated from each other. However, the criterion for verifying the type of optical adapter is not limited to the difference in the shape of the openings between the types of optical adapters. Alternatively, criteria to be described in conjunction with FIG. 24A to FIG. 31B may be adopted.

Figure 24A:
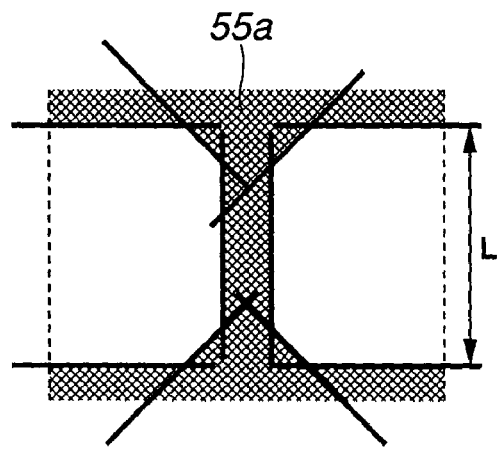
Figure 25:
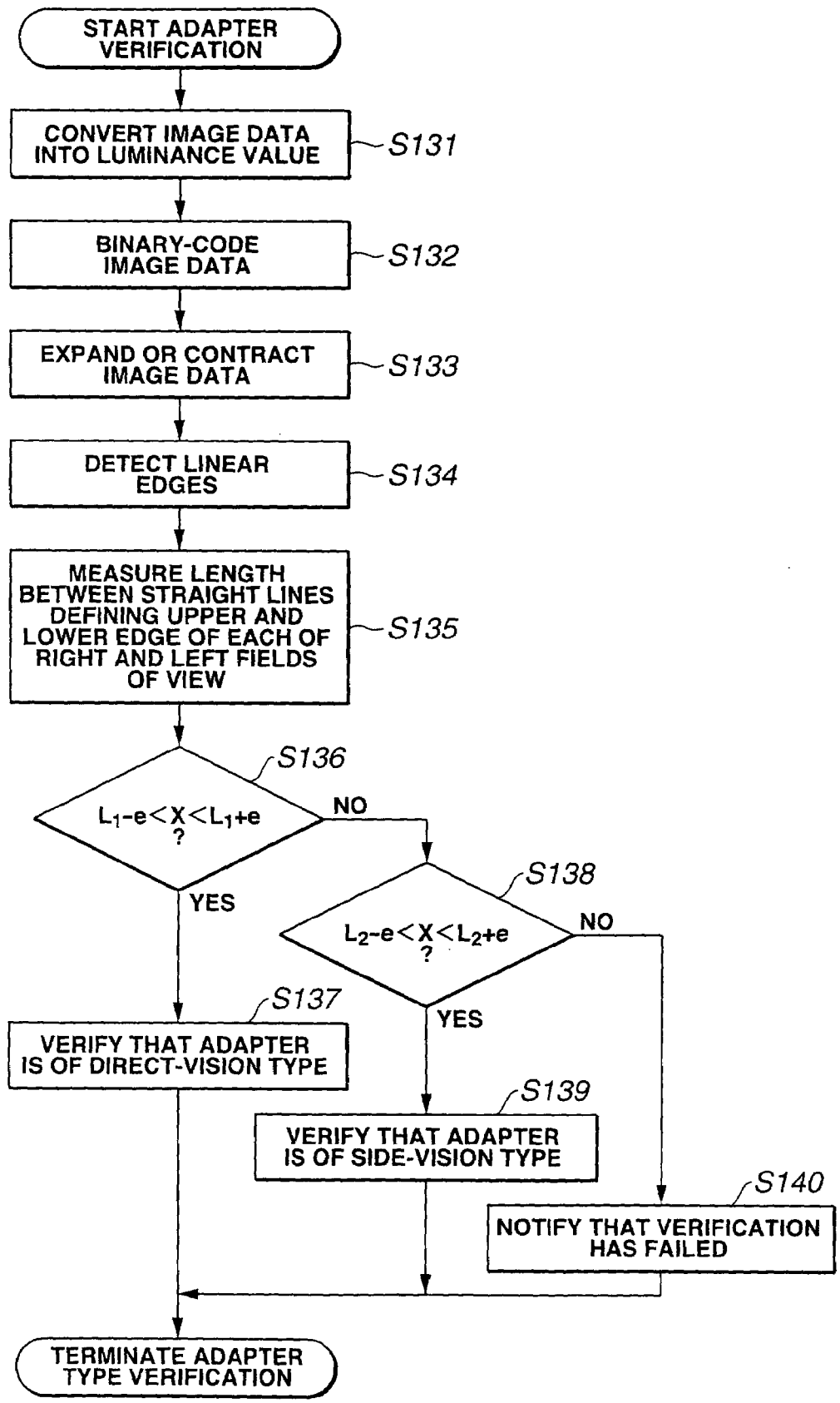

The criterion to be described in conjunction with FIG. 24A and FIG. 25 is a difference in the width in the vertical direction of the screen of the openings of a field mask serving as the identification section. The criterion to be described in conjunction with FIG. 26A to FIG. 31B is a difference in the shape and position of a projection of a field mask serving as the identification section. Herein, the image of the projection is compared with predetermined templates or matched with a template.

Referring to FIG. 24A and FIG. 25, a description will be made of a procedure of verifying the type of adapter in consideration of the difference in the width in the horizontal direction of the openings of a field mask.

Figure 24B:
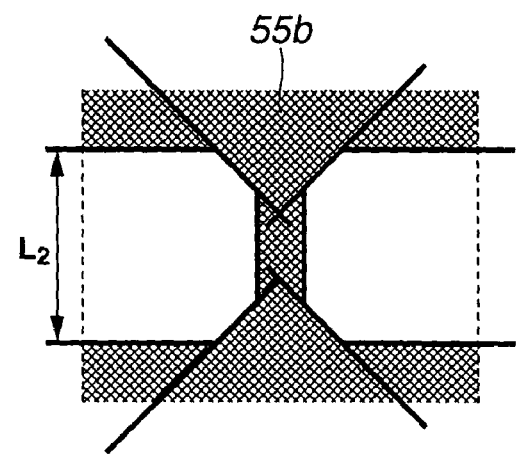
FIG. 24B is an explanatory diagram showing a field mask whose openings have a small width and which is adapted to a side-vision optical adapter.

As shown in FIG. 24A and FIG. 24B, according to the present embodiment, the openings of both the field masks 55a and 55b fixed to the respective optical systems included in the direct-vision stereoscopic optical adapter 7a and side-vision stereoscopic optical adapter 7b respectively have, for example, a hexagonal shape. However, the lengths L1 and L2 each of which is a length between two upper and lower straight lines extending in a horizontal direction has a relationship of L1>L2. The field mask 55a whose openings have the width thereof in the vertical direction of the screen set to the reference value L1 that is the length L1 is included in, for example, the direct-vision stereoscopic optical adapter 7a.

Referring to FIG. 25, a concrete procedure for verification will be described below.

First, image fetch is executed at step S113, and control is passed to step S114 of adapter type verification. In the adapter identification block 18a, the optical adaptor is identified and verified at the direction of the detection block 18b.

At the direction of the detection block 18b, at steps S131 to S133 described in FIG. 25, the image data is converted into luminance values, binary-coded, and expanded or contracted. At step S134, linear edges are detected as shown in FIG. 24A and control is passed to step S135. At step S135, straight lines limiting the upper and lower edges of each of the right and left fields of view are sampled, and the number of pixels lying between the straight lines is counted in order to measure the width X. After the width X is measured, processing is changed from that assigned to the detection block 18b to that assigned to the adapter type verification block 18c.

The adapter type verification block 18c compares the measured width X with the reference value L1 to see whether the measured width X falls within a predetermined range centered on the reference value L1 (±a tolerance e). When the width X falls within the range, that is, when L1−e<X<L1+e is established, control is passed to step S137. The direct-vision adapter notification screen image 5F shown in FIG. 23A is then displayed on the screen of the LCD 5, and adapter type verification is terminated.

On the other hand, when it is found at step S136 that the width X does not fall within the predetermined range centered on the reference value L1, control is passed to step S138. The width X is then compared with the reference value L2 indicating the side-vision type in order to check when the width X falls within a range limited by the difference and sum between the reference value L2 and a predetermined tolerance e. When the width X falls within the range, that is, when L2−e<X<L2+e is established, control is passed to step S139. The side-vision adapter notification screen image 5G shown in FIG. 23B is displayed on the screen of the LCD 5, and adapter type verification is terminated.

When it is found at step S138 that the width X does not fall within the predetermined range centered on the reference value L2, control is passed to step S140. The first warning display image 5C shown in FIG. 19 is displayed on the screen of the LCD 5. The failure in verification is notified, and adapter type verification is terminated.

The dimensions of the openings of each of the field masks are set to predetermined values so that the difference (L1−e) between the reference value L1 and the tolerance e will not equal the sum (L2+e) between the reference value L2 and the tolerance e.

As mentioned above, the difference in the width of the openings of a field mask in the horizontal direction of the openings is taken into consideration in order to verify whether the optical adapter attached to the distal section of the insertion unit is the direct-vision stereoscopic optical adapter or the side-vision stereoscopic optical adapter.

Incidentally, the shape of the openings of the field masks need not be hexagonal. Alternatively, the openings may have a rectangular shape but have different widths.

Referring to FIG. 26A to FIG. 28, a procedure of verifying the type of adapter by matching an image of an adapter with a template will be described below.

Figure 26A:
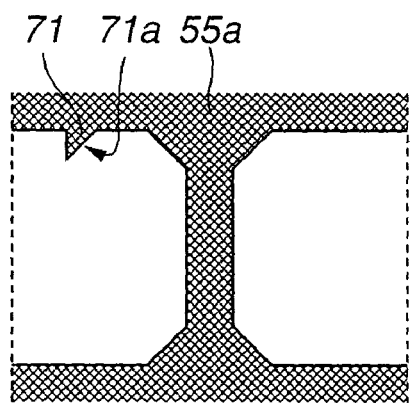
Figure 26B:
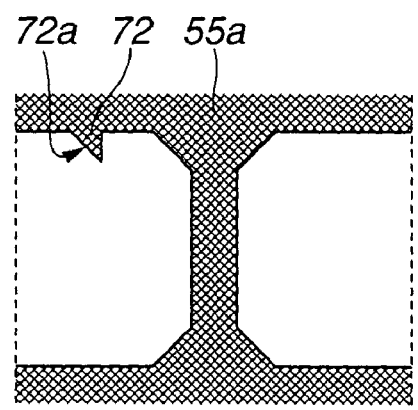
FIG. 26B is an explanatory diagram showing a field mask that has a projection indicating a side-vision optical adapter.

As shown in FIG. 26A and FIG. 26B, according to the present embodiment, the openings of both the field masks 55a and 55b included in the direct-vision stereoscopic adapter 7a and side-vision stereoscopic optical adapter 7b have a hexagonal shape. Triangular projections 71 and 72 having different shapes are formed to project into predetermined portions of the openings of the respective field masks, that is, project into the left openings of the respective field masks. The projections 71 and 72 have the oblique lines thereof located on different sides.

Figure 27A:
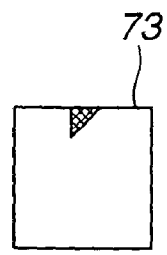
FIG. 27A shows a template that is matched with an image of the projection of the direct-vision optical adapter.
Figure 27B:
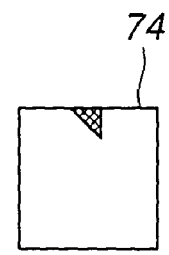
FIG. 27B shows a template that is matched with an image of the projection of the side-vision optical adapter.

A direct-vision verification template 73 shown in FIG. 27A is retrieved from, for example, the ROM 13, and superposed on the images of the left openings of the field masks 55a and 55b respectively in order to calculate correlation coefficients. Moreover, a side-vision verification template 74 shown in FIG. 27B is retrieved from the ROM 13, and superposed on the images of the left openings of the field masks 55a and 55b respectively in order to calculate correlation coefficients. At this time, the former correlation coefficients are different from the later correlation coefficients. Namely, the differences among the correlation coefficients are taken into consideration in order to verify whether the optical adapter attached to the insertion unit 20 is of the direct-vision type or the side-vision type.

A concrete procedure will be described with reference to FIG. 28.

First, image fetch is executed at step S113, and then control is passed to step S114 of adapter type verification. Identification and verification is executed at the direction of the detection block 18b included in the adapter identification block 18a.

Figure 28:
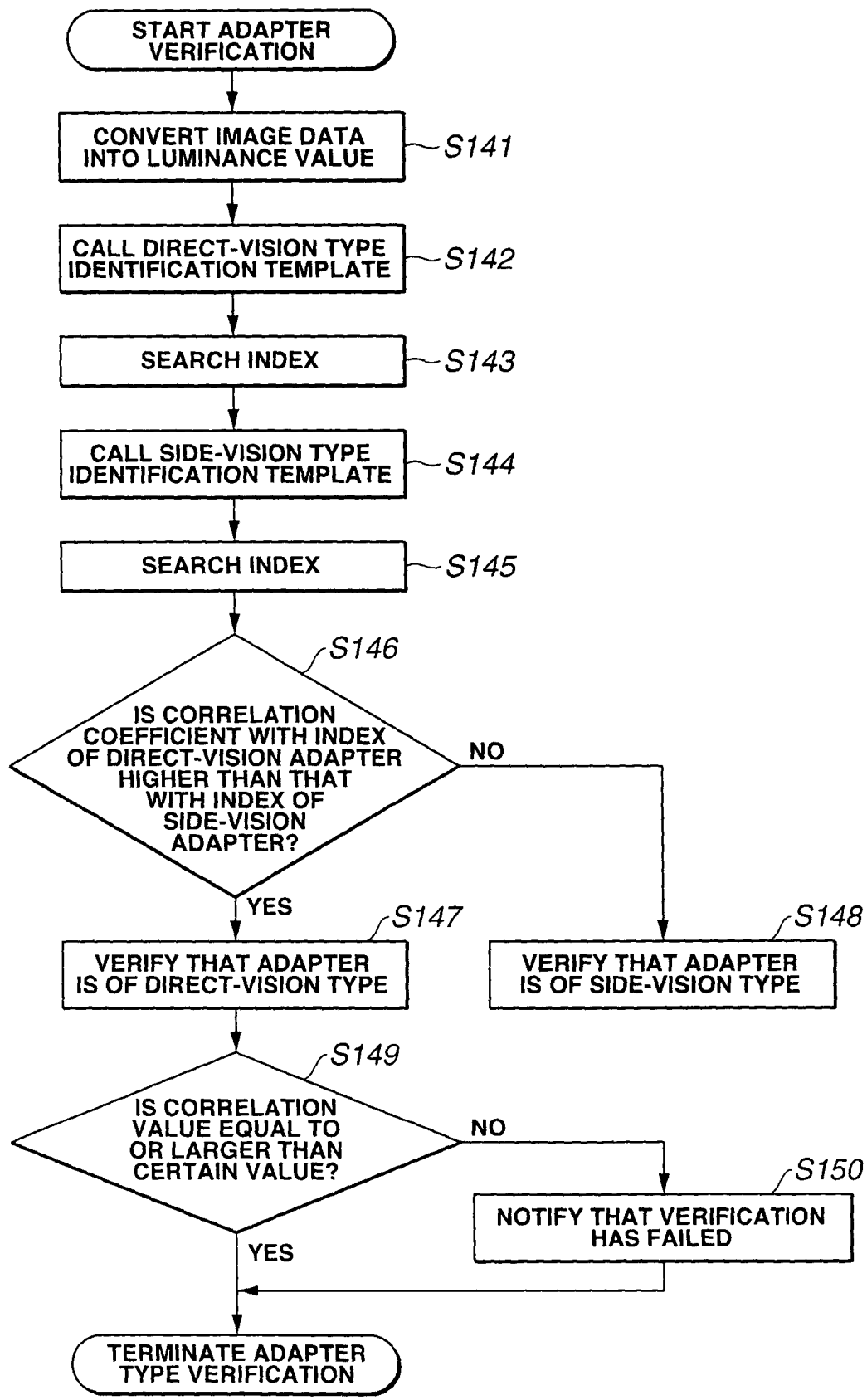

At the direction of the detection block 18b, first, image data is converted into luminance values at step S141 described in FIG. 28. Thereafter, at steps S142 and S143, the direct-vision verification template 73 is retrieved and superposed on the image of the projection 71. Thus, the template is matched with a projection in order to calculate a correlation coefficient. Thereafter, at steps S144 and S145, the side-vision verification template 74 is retrieved and superposed on the image of the projection 71. Thus, the template is matched with a projection in order to calculate a correlation coefficient.

At step S146, the correlation coefficient obtained using the direct-vision verification template 73 is compared with the correlation coefficient obtained using the side-vision verification template 74.

When the correlation coefficient obtained using the direct-vision verification template 73 is higher than the correlation coefficient obtained using the side-vision verification template 74, control is passed to step S147. It is verified tentatively that the attached optical adapter is of the direct-vision type. Control is then passed to step S149. On the other hand, the result of the comparison between the correlation coefficients is the reverse of the above, control is passed to step S148. It is verified tentatively that the attached optical adapter is of the side-vision type. Control is then passed to step S149.

At step S149, it is checked whether the correlation coefficients obtained using the templates are equal to or larger than a certain value. When it is found at step S149 that the correlation coefficients are equal to or larger than a certain value, the result of verification performed at step S147 or S148 is adopted. Namely, the direct-vision adapter notification screen image 5F or side-vision adapter notification screen image 5G shown in FIG. 23A or FIG. 23B is displayed on the screen of the LCD 5. Adapter type verification is then terminated.

When it is found at step S149 that the correlation coefficients obtained using the two templates fall below the certain value, control is passed to step S150. The first warning display image 5C shown in FIG. 19 is displayed on the screen of the LCD 5, and adapter type verification is terminated.

As mentioned above, the shape of the projection formed to project into a specific place in either of the openings formed in a field mask is verified by matching the image of the projection with a template. It can thus verified whether the optical adapter attached to the distal section of the insertion unit is the direct-vision stereoscopic optical adapter or the side-vision stereoscopic optical adapter.

Incidentally, the shape of the projections is not limited to the triangular shape but may be any other shape.

Moreover, the position at which the projection is formed is not limited to the upper side of the left opening.

Furthermore, the number of kinds of projections is not limited to 2 but may be larger than 2. The same number of templates as the number of kinds of projections should be stored in the ROM. All the templates are used to match the image of each projection with a template, and correlation coefficients are calculated. A template relative to which the projection exhibits the highest correlation coefficient is specified, whereby the type of optical adapter is verified.

Figure 29A:
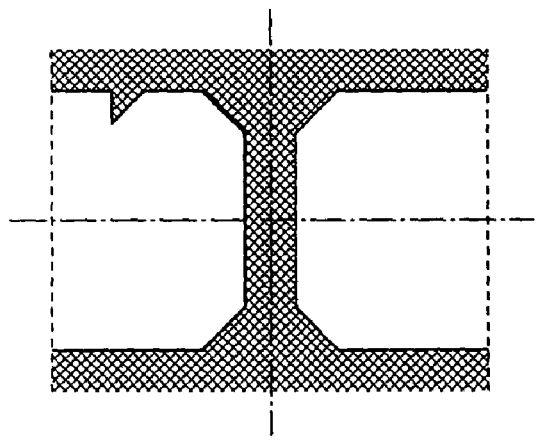
Figure 29B:
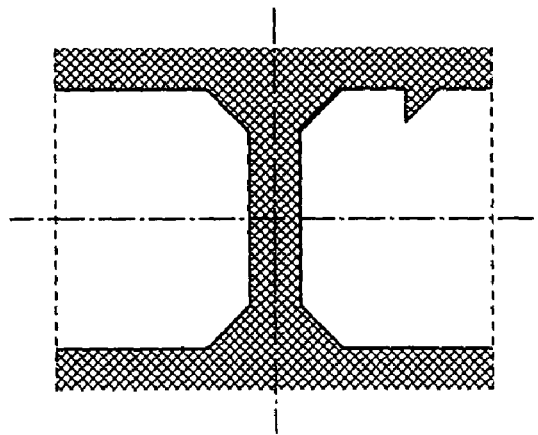
FIG. 29B is an explanatory diagram showing a field mask that has a projection indicating a side-vision optical adapter.

As shown in FIG. 29A and FIG. 29B, the projections may have the same shape and may be formed at different positions of different types of optical adapters. In this case, for example, the verification template 73 shown in FIG. 27A and formed to have a predetermined shape is used, as described in FIG. 30, to match the template with an image of a projection.

Figure 30:
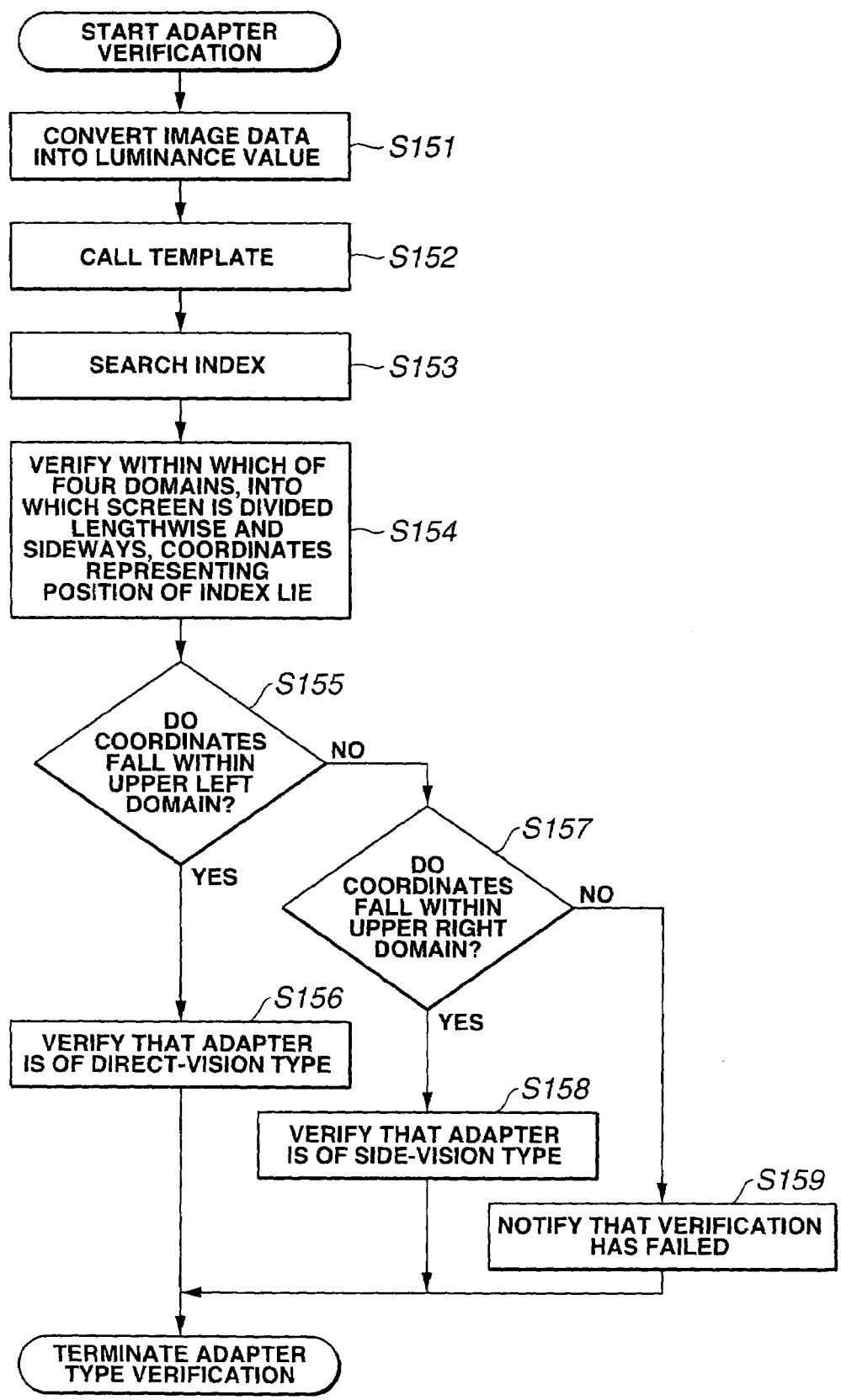

Specifically, image data is converted into luminance values at step S151 described in FIG. 30. Thereafter, at steps S152 and S153, the verification template is retrieved and matched with an image of a projection. Control is then passed to step S154 of detecting the position of the projection.

At step S154, it is checked in whichever of, for example, four areas, into which the screen is divided lengthwise and sideways, the position of the projection lies. The type of attached optical adapter is thus verified.

Specifically, it is checked at step S155 if the image of the projection appears on the upper left part of the screen. When it is found that the image of the projection appears on the upper left part of the screen as shown in FIG. 29A, control is passed to step S156. It is then verified that the attached optical adapter is of the direct-vision type.

On the other hand, when the image of the projection does not appear on the upper left part of the screen as shown in FIG. 29B, control is passed to step S157. It is then checked if the image of the projection appears on the upper right part of the screen. When it is found that the image of the projection appears on the upper right part of the screen, control is passed to step S158. It is then verified that the attached optical adapter is of the side-vision type. At this time, when the image of the projection does not appear on the upper right part of the screen, control is passed to step S159. The first warning display image 5C shown in FIG. 19 is displayed on the screen of the LCD 5, and adapter type verification is terminated.

Figure 31A:
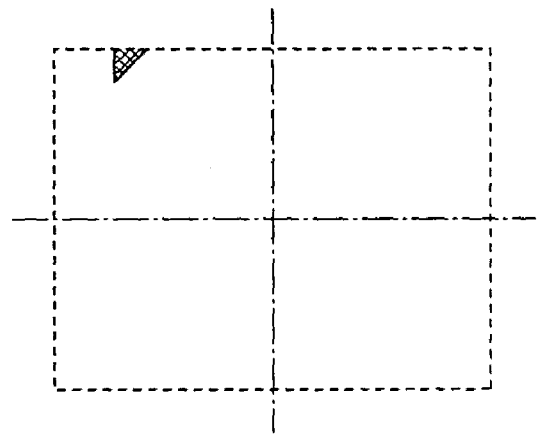
FIG. 31A and FIG. 31B show another structure for verifying the type of optical adapter by matching an image of an optical adapter with a template.
Figure 31B:
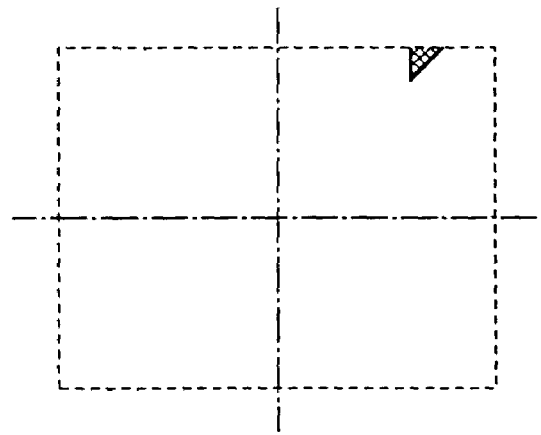

As shown in FIG. 31A and FIG. 31B, only the image of the projection may be displayed on the screen. In whichever of the areas the image of the projection lies may then be detected in order to verify the type of optical adapter.

Incidentally, stereoscopic measurement may be achieved by using a liquid crystal shutter to switch two images that are produced with different fields of view, and to thus display the images alternately. Even in this case, it can be verified whether the stereoscopic adapter attached to the insertion unit is of the direct-vision type or side-vision type.

Now, a second embodiment will be described with reference to drawings.

Figure 32:
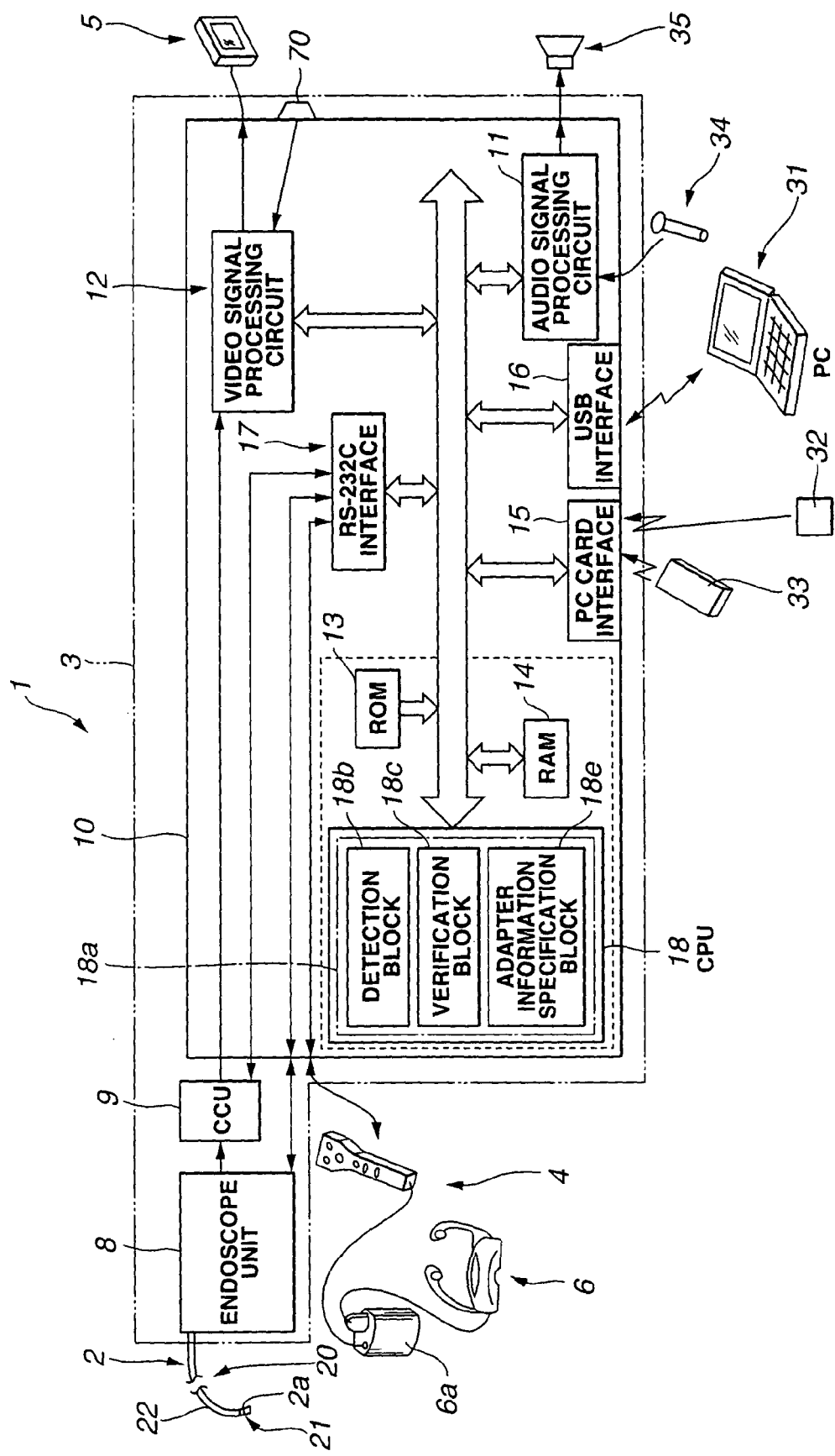
FIG. 32 to FIG. 34 are explanatory diagrams concerning a second embodiment of the present invention.

As shown in FIG. 32, according to the present embodiment, the adapter identification block 18a included in the CPU 18 has an adapter information specification block 18e on behalf of the result-of-verification notification block 18d included in the first embodiment. The other components are identical to those of the first embodiment. The same reference numerals will be assigned to the same members, and the description of the members will be omitted.

The adapter information specification block 18e reads adapter information by selecting the adapter information from among adapter information items, which are stored in association with types of adapters in the ROM 13 or the like in advance, according to the result of verification received from the adapter type verification block 18c, and then specifies the adapter information.

Figure 33:
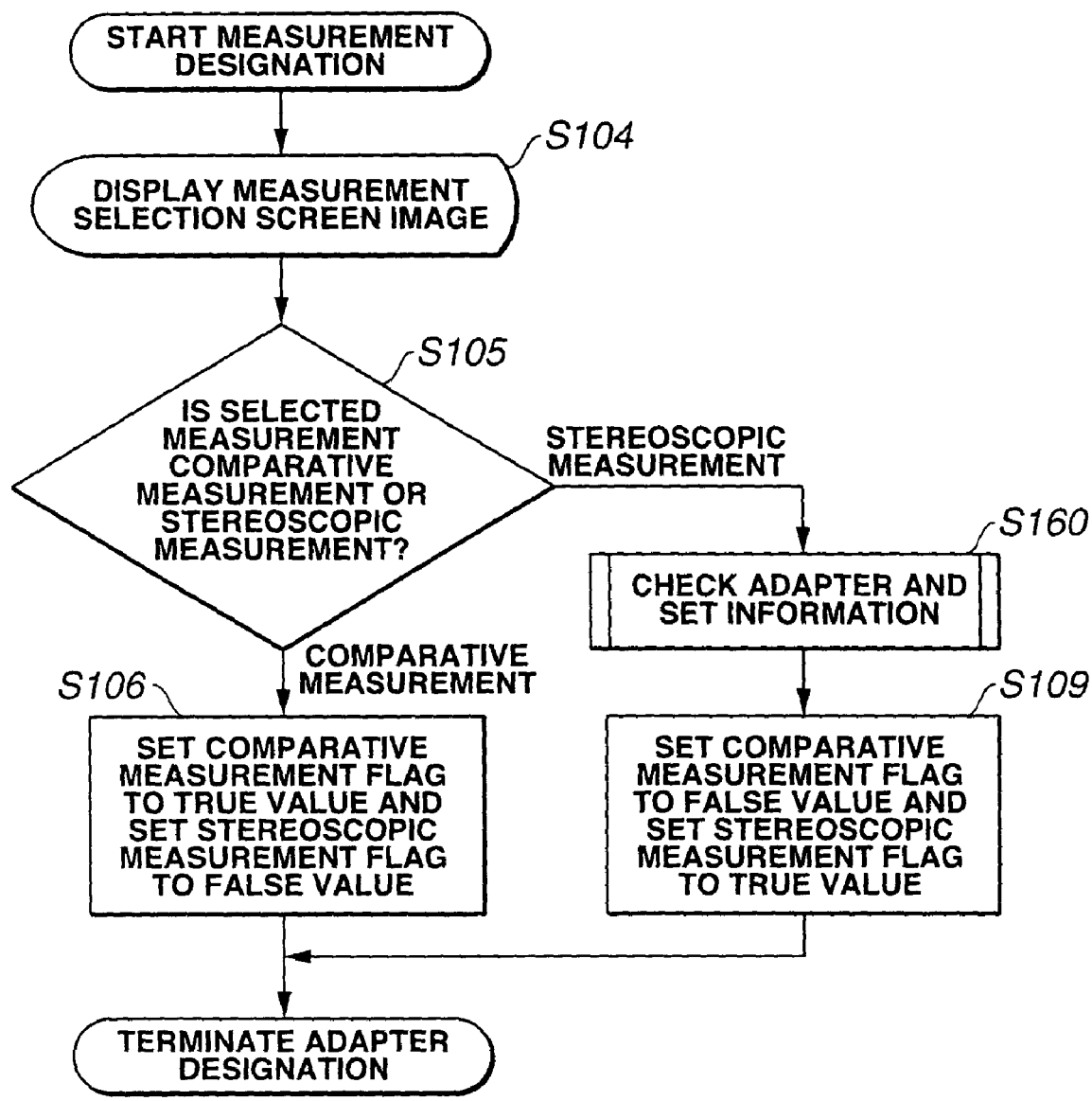

According to the present embodiment, as described in FIG. 33, when stereoscopic measurement is selected at step S105, control is passed to step S160 and adapter verification and information specification is performed. At the next step S109, the stereoscopic measurement flag is set to the TRUE value and control is passed to the main loop.

Figure 34:
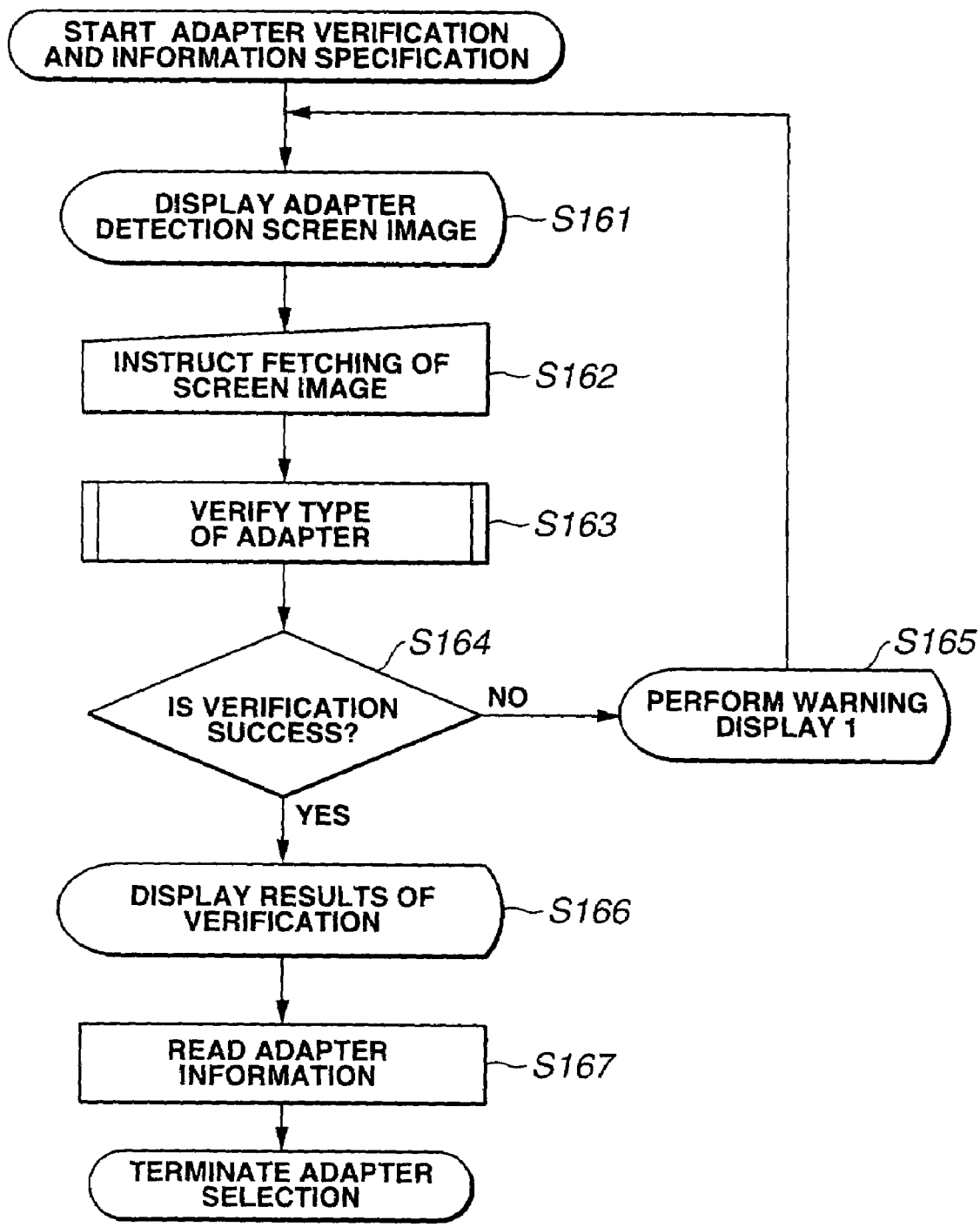

Referring to FIG. 34, a sequence of adapter verification and information specification will be described below.

First, when it is found at step S105 that stereoscopic measurement has been selected, an endoscopic image of the field mask included in the stereoscopic optical adapter 7a or 7b attached to the distal section 21 is displayed on the screen of the LCD 5 at step 161. Control is then passed to step S162. After the endoscopic image is fetched at step S162, control is passed to step S163. The type of optical adapter is verified as described in conjunction with FIG. 21, FIG. 25, FIG. 28, and FIG. 30.

Thereafter, it is checked at step S164 if adapter type verification has succeeded. When it is found at step S164 that adapter type verification has failed because of a failure in fetching of a white image at step S162, the first warning display image 5C shown in FIG. 19 is displayed on the screen of the LCD 5. Control is then returned to step S161.

On the other hand, when it is found at step S164 that adapter type verification has succeeded, control is passed to step S166. The display image 5F or 5G shown in FIG. 23A or FIG. 23B is displayed on the screen of the LCD 5. An operator is notified whether the optical adapter attached to the insertion unit 20 is of the direct-vision type or side-vision type. Thereafter, at step S167, the adapter information specification block 18e reads adapter information concerning the optical adapter designated with the result of verification from the ROM 13, and specifies the adapter information. Adapter verification and information specification is then terminated.

As mentioned above, when a user selects stereoscopic measurement with the optical adapter attached to the insertion unit, the CPU verifies the type of optical adapter attached to the insertion unit according to a predetermined program. Moreover, adapter information concerning the optical adapter is read and specified. Thus, stereoscopic measurement can be performed with adapter information concerning the attached optical adapter specified all the time.

The preferred embodiments of the present invention have been described with reference to the accompanying drawings. It should be understood that the present invention is not limited to the precise embodiments but any skilled person in the art can make various changes and modifications of the present invention without departing from the spirit or scope of the invention defined in the appended claims.

What is claimed is:

1. An endoscope system comprising:
an electronic endoscope including an imaging unit;
a plurality of types of optical adapters each of which is freely detachably attached to the distal section of the electronic endoscope, and each having a predetermined observational optical system that includes an identification section with which the type of optical adapter can be identified;
a control device that is electrically connected to the electronic endoscope and that includes an optical adapter identifying/verifying facility that detects the identification section so as to verify the type of optical adapter, an image processor that receives an imaging signal sent from the imaging unit so as to produce a video signal, and a controller that manipulates a video signal produced by the image processor, and controls the electronic endoscope and external equipment; and
a display device that receives the video signal sent from the control device and displays an image represented by the video signal.

2. An endoscope system according to claim 1, wherein: the control device further includes at least one of a result-of-verification notifying facility which notifies a user of the result of verification sent from the optical adapter identifying/verifying facility, and an adapter information specification block that reads adapter information by selecting the adapter information from among adapter information items, which are registered in advance in association with types of optical adapters, according to the result of verification sent from the optical adapter identifying/verifying facility, and specifies the adapter information.

3. An endoscope system according to claim 1, wherein the identification section is a field mask included in the observational optical system incorporated in the optical adapter.

4. An endoscope system according to claim 3, wherein the shape of the openings formed in the field mask is varied depending on the type of optical adapter.

5. An endoscope system according to claim 4, wherein the optical adapter identifying/verifying facility includes: a detection block that detects the number of straight lines defining an image of each of the openings formed in the field mask which is displayed on the display device; and an adapter type verification block that compares the number of straight lines detected by the detection block with reference values that are registered in advance so as to verify the type of optical adapter.

6. An endoscope system according to claim 3, wherein the width of the openings formed in the field mask is varied depending on the type of optical adapter.

7. An endoscope system according to claim 6, wherein the optical adapter identifying/verifying means includes: a detection block that selects straight lines close to horizontal lines from among straight lines defining an image of each of the openings of a field mask displayed on the display device, and calculating the length between the straight lines; and an adapter type verification block for comparing the length calculated by the detection block with reference values, which are registered in advance, so as to verify the type of optical adapter.

8. An endoscope system according to claim 3, wherein the shape of the projection of the field mask projecting into an opening is varied depending on the type of optical adapter.

9. An endoscope system according to claim 3, wherein the position of the projection of the field mask projecting into an opening is varied depending on the type of optical adapter.

10. An endoscope system according to claim 8, wherein the optical adapter identifying/verifying means includes: a detection block that calculates the correlation coefficients of the image of the projection of the field mask, which projects into an opening, displayed on the display device relative to a plurality of templates associated with the optical adapters and registered in advance; and an adapter type verification block that samples a template relative to which the highest correlation coefficient is calculated by the detection block so as to verify the type of optical adapter.

11. An endoscope system according to claim 9, wherein the optical adapter identifying/verifying means includes: a detection block that calculates the correlation coefficients of the image of the projection of the field mask, which projects into an opening, displayed on the display device relative to a plurality of templates associated with the optical adapters and registered in advance; and an adapter type verification block that samples a template relative to which the highest correlation coefficient is calculated by the detection block so as to verify the type of optical adapter.

* * * * *